US006809182B2

(12) United States Patent
Silverstein et al.

(10) Patent No.: US 6,809,182 B2
(45) Date of Patent: Oct. 26, 2004

(54) VZV ORF29P PROTEIN-RELATED COMPOSITIONS AND METHODS

(75) Inventors: Saul J. Silverstein, Irvington, NY (US); Paula W. Annuziato, Larchmont, NY (US); Anne A. Gershon, New York, NY (US); Octavian Lungu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/769,699

(22) Filed: Jan. 25, 2001

(65) Prior Publication Data

US 2001/0039051 A1 Nov. 8, 2001

Related U.S. Application Data

(60) Provisional application No. 60/177,901, filed on Jan. 25, 2000.

(51) Int. Cl.[7] .................... C07K 14/00; A61K 38/00; C12N 15/09; C12Q 1/68

(52) U.S. Cl. .................... 530/358; 530/350; 424/460; 424/450; 514/2; 514/44; 435/6; 435/29; 435/455; 435/468; 435/320.1; 435/235.1

(58) Field of Search .............................. 435/6, 29, 455, 435/468, 320.1, 235.1; 530/350, 358; 514/2, 44; 424/460, 450

(56) References Cited

U.S. PATENT DOCUMENTS 5,674,980 A * 10/1997 Frankel et al. .............. 530/350

OTHER PUBLICATIONS

Berendsen, Herman J. Science, Oct. 23, 1998, vol. 282, pp. 642–643.*
Schwartz, H. James. 1981. biochemical Control Mechanisms in Synaptic Transmission, p. 121–131. In E.R. Kandel and J.H. Schwartz, Principles of Neural Science, Edward Arnold Publishers, New York, NY. (Exhibit 2).
Annunziato, P., O. Lungu, A. Gershon, D. Silvers, P. LaRussa, and S. Silverstein. 1996. In situ hybridization detection of varicella zoster virus in paraffin–embedded skin biopsy samples. Clin. Diagn. Virol. 7:69–76. (Exhibit 1).
Arvin, A. 1996. Varicella–zoster virus, p. 2547–2585. In B.N. Fields, D.M. Knipe, and P.M. Howley (ed.), Fields virology, 3$^{rd}$ ed., vol. 2. Lippincott–Raven Publishers, Philadelphia, Pa. (Exhibit 2).
Asano, Y., N. Itakura, Y. Hiroishi, S. Hirose, T. Nagai, T. Ozaki, T. Yazaki, Y. Yamanishi, and M. Takahashi. 1985. Viremia is present in incubation period in nonimmunocomprised children with varicella. J. Pediatr. 106: 69–71. (Exhibit 3).

Assouline, J.G., M. J. Levin, E. O. Major, B. Forghani, S. Straus, and J.M. Ostrove. 1990. Varicella–zoster virus infection of human astrocytes, Schwann cells, and neurons. Virology 179:834–843. (Exhibit 4).
Cohen, J., and S. Straus. 1996. Varicella–zoster virus and its replication, p. 2525–2546. In B. N. Fields, D.M. Knipe, and P.M. Howley (ed.), Fields virology, 3$^{rd}$ ed., vol. 2. Lippincott–Raven Publishers, Philadelphia, PA. (Exhibit 5).
Cohrs, R.J., M. Barbour, and D. Gilden. 1996. Varicella-zoster virus (VZV) transcription during latency in human ganglia: detection of transcripts mapping to genes 21,29,62, and 63 in a cDNA library enriched for VZV RNA. J. Virol. 70:2789–2796. (Exhibit 6).
Cohrs, R.J., M.B. Barbour, R. Mahlingham, M. Wellish, and D. Gilden. 1995. Varicella–zoster virus (VZV) transcription during latency in human ganglia: prevalence of VZV gene 21 transcripts in latently infected human ganglia. J. Virol. 69:2674–2678. (Exhibit 7).
Cohrs, R.J., K. Srock, M.B. Barbour, G. Owens, R. Mahlingham. M. Devlin. M. Wellish, and D. Gilden. 1994. Varicella–zoster virus (VZV) transcription during latency in human ganglia: construction of a cDNA library from latently infected human trigeminal ganglia and detection of a VZV transcript. J. Virol. 68:7900–7908. (Exhibit 8).
Croen, K.D., J.M. Ostrove, L.Y. Dragovic, and S.E. Straus, 1988. Patterns of gene expression and sites of latency in human ganglia are different for varicella–zoster and herpes simplex viruses. Proc. Natl. Acad. Sci. USA 85:9773–9777. (Exhibit 9).
Esiri, M., and A. Tomlinson. 1972. Herpes zoster: demonstration of virus in trigeminal nerve and ganglion by immunofluorescence and electron micros–copy. J. Neurol. Sci. 15:35–48. (Exhibit 10).
Hope–Simpson, R.E. 1965. The nature of herpes zoster: a long term study and a new hypothesis. Proc. R. Soc. Med. 58:9–20. (Exhibit 11).

(List continued on next page.)

*Primary Examiner*—Gerry Leffers
(74) *Attorney, Agent, or Firm*—John P. White; Cooper & Dunham LLP

(57) ABSTRACT

The present invention provides compositions of matter comprising 29p protein having bound thereto an agent whose delivery into a eukaryotic cell is desired. The present invention also provides a monoclonal antibody which specifically binds to 29p protein. The present invention further provides methods for delivering an agent into a eukaryotic cell, and methods for causing a eukaryotic cell to secrete a desired protein in the form of a fusion protein. The present invention further provides 29p protein-containing pharmaceutical compositions. The present invention still further provides nucleic acid molecules which hybridize to at least a portion of a nucleic acid molecule encoding 29p protein. Finally, the present invention provides methods for detecting the presence of, and quantitatively determining the amount of, a 29p protein-encoding nucleic acid molecule in a sample.

4 Claims, 28 Drawing Sheets-

OTHER PUBLICATIONS

Kennedy, P., E. Grinfeld, and J. Gow. 1998. Latent varicella–zoster virus is located predominantly in neurons in human trigeminal ganglia. Proc. Natl. Acad. Sci. USA 95:4658–4662. (Exhibit 12).

Kinchington, P., J. Hougland, A. Arvin. W. Ruyechan, and J. Hay 1992. The varicella–zoster virus immediate–early protein IE62 is a major component of virus particles. J. Virol. 66:359–366. (Exhibit 13).

Kinchington, P.R., D. Bookey, and S.E. Turse. 1995. The transcriptional regulatory proteins encoded by varicella-zoster virus open reading frames (ORFs) 4 and 63, but not ORF 61, are associated with purified virus particles. J. Virol. 69:4274–4282. (Exhibit 14).

Kinchington, P.R., P. Ling, M. Pensiero, W.T. Ruyechan, and J. Hay. 1990. The glycoprotein products of varicella–zoster virus gene 14 and their defective accumulation in a vaccine strain (Oka). J. Virol. 64:4540–4548. (Exhibit 15).

Koropchak, C., G. Graham, J. Palmer, M. Winsberg, S. Ting, M. Wallace, C. Prober, and A. Arvin. 1991. Investigation of varicella–zoster virus infection by polymerase chain reaction in the immunocompetent host with acute varicella. J. Infect. Dis. 163:1016–1022 (Exhibit 16).

Lungu, O., P. Annunziato, A. Gershon, S. Stegatis, D. Josefson, P. LaRussa, and S. Silverstein. 1995. Reactivated and latent varicella–zoster virus in human dorsal root ganglia, Proc. Natl. Acad. Sci. USA 92:10980–10984. (Exhibit 17).

Lungu, O., C. Panagiotidis, P. Annunziato, A. Gershon, and S. Silverstein. 1998. Aberrant intracellular localization of varicella–zoster virus regulator proteins during latency. Proc. Natl. Acad. Sci. USA 95:7080–7085. (Exhibit 18).

Mahalingam, R., M. Wellish, R. Cohrs, S. Debrus, J. Piette, B. Rentier, and D. Gilden. 1996. Expression of protein encoded by varicella–zoster virus open reading frame 63 in latently infect human ganglionic neurons. Proc. Natl. Acad. Sci. USA 93:2122–2124. (Exhibit 19).

Mainka, C., B. Fuss, H. Geiger, H. Hofelmayr, and M. Wolff. 1998. Characterization of viremia at different stages of varicella–zoster virus infection. J. Med. Virol. 56:91–98. (Exhibit 20).

Mazur, H., and R. Dolin. 1978. Herpes zoster at the NIH: a 20 year experience. Am. J. Med. 65:738–744. (Exhibit 21).

Meier, J. L., R. P. Holman, K. D. Croen, J.E. Smialek, and S.E. Strauss. 1993. Varicella–zoster virus transcription in human trigeminal ganglia. Virology 193:193–200. (Exhibit 22).

Nikkels, A., P. Delvenne, S. Debrus, C. Sadzot–Delaux, J. Piette, B. Rentier, and G. Pierard. 1995. Distribution of varicella–zoster virus gpI and gpII and corresponding genome sequences in the skin. J. Med. Virol. 46:91–6. (Exhibit 23).

Nikkels, A.F., B. Rentier, and G.E. Pierard. 1997. Chronic varicella–zoster virus skin lesions in patients with human immunodeficiency virus are related to decreased expression of gE and gB. J. Infect. Dis. 176:261–264. (Exhibit 24).

Nikkels, A.F., S. Debrus, C. Sadzot–Delvaux, J. Piette, P. Delvenne, B. Rentier, and G.E. Pierard. 1993. Comparative immunohistochemical study of herpes simplex and varicella–zoster infections. Circhows Arch. A 422:121–126. (Exhibit 25).

Sadzot–Delvaux, C., M.–P. Merville–Louis, P. Delree, P. Marc, G. Moonen, and B. Rentier. 1990. An in vivo model of varicella–zoster virus latent infection of dorsal root ganglia. J. Neurosci. Res. 26:83–89 (Exhibit 26).

Sawyer, M.H., Y.N. Wu, C.J. Chamberlin, C. Burgos, S.K. Brodine, W.A. Bowler, A. LaRocco, E.C. Oldfield, and M. R. Wallace. 1992. Detection of varicella–zoster DNA in the oropharynx and blood of patients with varicella. J. Infect. Dis. 166:885–888 (Exhibit 27).

* cited by examiner

FIGURE 6-1

```
    9            18            27            36            45            54
5' ATG GAA AAT ACT CAG AAG ACT GTG CCC ACG GGG CCC CTG GGT TAC GTT
    M   E   N   T   Q   K   T   V   P   T   G   P   L   G   Y   V 63            72            81            90            99           108
   TAT GCG TGC CGG GTT GAA GAT CTG GAG GAA ATT TCA TTT TTG GCC GCT
    Y   A   C   R   V   E   D   L   E   E   I   S   F   L   A   A 117           126           135           144           153           162
   CGT AGC ACG GAC TCT GAT TTG GCT TTA CCT TTG ATG CGT AAT TTG ACC GTG
    R   S   T   D   S   D   L   A   L   P   L   M   R   N   L   T   V 171           180           189           198           207           216
   GAA AAA ACT TTT ACA TCC AGC CTG GCG GTG GTT TCT GGA GCA CGC ACT ACG GGT
    E   K   T   F   T   S   S   L   A   V   V   S   G   A   R   T   T   G 225           234           243           252           261           270
   CTT GCC GGA GCT GGT ATT ACC TTA AAA CTC ACT ACC AGT CAT TTC TAT CCA TCT
    L   A   G   A   G   I   T   L   K   L   T   T   S   H   F   Y   P   S 279           288           297           306           315           324
   GTC TTT CAC GGA AAA GGC AAA CAC GTT TTA CCC AGC TCC GCG GCC CCA AAT
    V   F   H   G   K   G   K   H   V   L   P   S   S   A   A   P   N
```

FIGURE 6-2

```
     333         342         351         360         369         378
CTC ACA CGC GCG TGT AAC GCG GCT CGA GAA CGG TTT GGG TTT TCA CGC TGC CAA
 L   T   R   A   C   N   A   A   R   E   R   F   G   F   S   R   C   Q 387         396         405         414         423         432
GGG CCT GTT GAC GGT GCT GTT GAG ACG ACC GGC GCT GAG ATA TGC ACC CGC
 G   P   V   D   G   A   V   E   T   T   G   A   E   I   C   T   R 441         450         459         468         477         486
CTT GGA TTA GAG CCA GAA AAT ACA ATA TTA TAC TTG GTC ACG GCA TTG TTT
 L   G   L   E   P   E   N   T   I   L   Y   L   V   T   A   L   F 495         504         513         522         531         540
AAG GAA GCC GTA ATG TGC AAC GTG TTT CTG CAT TAT GGA CTC GAT ATT
 K   E   A   V   M   C   N   V   F   L   H   Y   G   L   D   I 549         558         567         576         585         594
GTT CAT ATT AAC CAT GGG GAT GTT ATA CGT TAT GAA CCG TTA TTT CCG GTA CAA CTT
 V   H   I   N   H   G   D   V   I   R   Y   E   P   L   F   P   V   Q   L 603         612         621         630         639         648
TTC ATG CCC GAT AAC CGT CTG GTA CCC GAC TTC AAC ACT CAT CAC AGG
 F   M   P   D   N   R   L   V   P   D   F   N   T   H   H   R
```

FIGURE 6-3

```
     657                666         675         684         693         702
TCT ATC GGA GAG GGT TTT GTA TAC CCA ACA CCC TTT TAT AAC ACC GGG TTG TGC
 S   I   G   E   G   F   V   Y   P   T   P   F   Y   N   T   G   L   C 711                720         729         738         747         756
CAT TTA ATA CAT GAC TGT GTT ATT GCT CCC ATG GCC GTT GCC TTG CGC GTC AGA
 H   L   I   H   D   C   V   I   A   P   M   A   V   A   L   R   V   R 765                774         783         792         801         810
AAT GTA ACT GCC GTC GCC CGA GGA GCG GCC CAC CTT GCT TTT GAT GAA AAT CAC
 N   V   T   A   V   A   R   G   A   A   H   L   A   F   D   E   N   H 819                828         837         846         855         864
GAG GGG GCA GTA CTC CCC GAC ATT ACG TAC ACG TAT TTT CAG TCC TCT TCA
 E   G   A   V   L   P   P   D   I   T   Y   T   Y   F   Q   S   S   S 873                882         891         900         909         918
AGT GGA ACC ACT ACC GCC CGT GGA GCG CGT CGA AAC GAT GTC AAC TCC ACG TCT
 S   G   T   T   T   A   R   G   A   R   R   N   D   V   N   S   T   S 927                936         945         954         963         972
AAG CCT AGC CCA TCG GGG GGG TTT GAA AGA CGG TTG GCG TCT ATT ATG GCC GCT
 K   P   S   P   S   G   G   F   E   R   R   L   A   S   I   M   A   A
```

FIGURE 6-4

```
      981         990         999         1008        1017        1026
GAC ACA GCC TTG CAC GCA GAA GTT ATA TTC AAC ACT GGA ATT TAC GAA GAA ACT
 D   T   A   L   H   A   E   V   I   F   N   T   G   I   Y   E   E   T 1035        1044        1053        1062        1071        1080
CCA ACA GAT ATC AAA GAA TGG CCA ATG TTT ATA GGC ATG GAG GGC ACT TTG CCA
 P   T   D   I   K   E   W   P   M   F   I   G   M   E   G   T   L   P 1089        1098        1107        1116        1125        1134
AGG CTA AAC GCT CTG GGG TCA TAT ACC GCT CGT GTG GCC GGG GTC ATT GGT GCG
 R   L   N   A   L   G   S   Y   T   A   R   V   A   G   V   I   G   A 1143        1152        1161        1170        1179        1188
ATG GTT TTC AGC CCA AAT TCT GCG TTG TAT CTA ACT GAG GTG GAG GAT AGC GGG
 M   V   F   S   P   N   S   A   L   Y   L   T   E   V   E   D   S   G 1197        1206        1215        1224        1233        1242
ATG ACC GAA GCC AAG GAT GGG GGA CCG CCA TCA TTT AAT CGA TTT TAC CAG
 M   T   E   A   K   D   G   G   P   P   S   F   N   R   F   Y   Q 1251        1260        1269        1278        1287        1296
TTT GCC GGA CCT CAT TTA GCT GCG AAT CCC CAA ACA GAT CGA GAT GGC CAC GTT
 F   A   G   P   H   L   A   A   N   P   Q   T   D   R   D   G   H   V 1305        1314        1323        1332        1341        1350
CTA TCC AGT CAG TCT ACG GGT TCA AAC ACA GAG TTT AGC GTG GAT TAT TTG
 L   S   S   Q   S   T   G   S   N   T   E   F   S   V   D   Y   L
```

FIGURE 6-5

```
     1359           1368           1377           1386           1395           1404
GCA CTC ATT TGT GGA TTT GGA GCA CCC CTG TTG GCG CGA CTG CTT TTT TAT CTA
 A   L   I   C   G   F   G   A   P   L   L   A   R   L   L   F   Y   L 1413           1422           1431           1440           1449           1458
GAA CGC TGT GAC GCT GGT GCG TTT ACA GGG GGT CAC GGG GAT GCG TTA AAA TAT
 E   R   C   D   A   G   A   F   T   G   G   H   G   D   A   L   K   Y 1467           1476           1485           1494           1503           1512
GTT ACG GGG ACC TTT GAC TCT GAA ATT CCA TGT AGT TTA TGT GAA AAA CAC ACG
 V   T   G   T   F   D   S   E   I   P   C   S   L   C   E   K   H   T 1521           1530           1539           1548           1557           1566
CGG CCG GTA TGC GCT CAC ACA ACA GTA CAC CTT AGA CTT GGA ACA ATG CCG CGA
 R   P   V   C   A   H   T   T   V   H   R   L   R   Q   R   M   P   R 1575           1584           1593           1602           1611           1620
TTT GGA CAA GCC ACC CGT CAA CCT ATT GGG GTG TTT GGA ACA ATG AAC AGC CAA
 F   G   Q   A   T   R   Q   P   I   G   V   F   G   T   M   N   S   Q 1629           1638           1647           1656           1665           1674
TAT AGC GAC TGC GAT CCT CTA GGA AAC TAT GCT CCA TAT TTA ATC CTT CGA AAA
 Y   S   D   C   D   P   L   G   N   Y   A   P   Y   L   I   L   R   K 1683           1692           1701           1710           1719           1728
CCC GGG GAT CAA ACG GAA GCA GCA AAG GCA ACC ATG CAG GAC ACT TAT AGG GCT
 P   G   D   Q   T   E   A   A   K   A   T   M   Q   D   T   Y   R   A
```

FIGURE 6-6

```
     1737           1746           1755           1764           1773           1782
ACA CTA GAA CGC TTG TTT ATC GAT CTA GAA CAA GAG CGA CTA CTG GAT CGC GGT
 T   L   E   R   L   F   I   D   L   E   Q   E   R   L   L   D   R   G
     1791           1800           1809           1818           1827           1836
GCC CCA TGT TCT TCC GAG GGA CTA TCG TCT GTC ATT GTC GAT CAT CCA ACG TTT
 A   P   C   S   S   E   G   L   S   S   V   I   V   D   H   P   T   F
     1845           1854           1863           1872           1881           1890
CGT CGC ATA TTA GAC ACA CTG CGT GCG CGT ATA GAA CAG ACA ACA CAA TTT
 R   R   I   L   D   T   L   R   A   R   I   E   Q   T   T   Q   F
     1899           1908           1917           1926           1935           1944
ATG AAA GTG TTG GTT GAG ACC CGC GAT TAT AAG ATC CGT GAA GGA TTA TCC GAA
 M   K   V   L   V   E   T   R   D   Y   K   I   R   E   G   L   S   E
     1953           1962           1971           1980           1989           1998
GCC ACC CAT TCA ATG GCG TTA ACG TTT GAT CCA TAC TCA GGA GCA TTT TGT CCC
 A   T   H   S   M   A   L   T   F   D   P   Y   S   G   A   F   C   P
     2007           2016           2025           2034           2043           2052
ATT ACC AAT TTT TTA GTT AAA CGA ACA CAC CTA GCC GTG GTA CAA GAC TTA GCA
 I   T   N   F   L   V   K   R   T   H   L   A   V   V   Q   D   L   A
```

FIGURE 6-7

```
      2061              2070              2079              2088              2097              2106
TTA AGC CAA TGT CAT TGT GTA TTT TAC GGA CAG CAA GTT GAG GGG CGG AAC TTT
 L   S   Q   C   H   C   V   F   Y   G   Q   Q   V   E   G   R   N   F 2115              2124              2133              2142              2151              2160
CGT AAC CAA TTC CAA CCT GTT TTG CGG CGG CGT TTT GTT GAC CTG TTT AAT GGG
 R   N   Q   F   Q   P   V   L   R   R   R   F   V   D   L   F   N   G 2169              2178              2187              2196              2205              2214
GGG TTT ATA TCA ACA CGC TCT ATA ACC GTA ACA TTA TCT GAA GGT CCT GTA TCC
 G   F   I   S   T   R   S   I   T   V   T   L   S   E   G   P   V   S 2223              2232              2241              2250              2259              2268
GCC CCA AAT CCG ACA TTG GGA CAA GAC GCG CCC GCG GGG CGT ACC TTT GAT GGG
 A   P   N   P   T   L   G   Q   D   A   P   A   G   R   T   F   D   G 2277              2286              2295              2304              2313              2322
GAT TTA GCG CGC GTA AGC GTG GAA GTT ATT CGG GAT ATA CGA GTT AAA AAT AGG
 D   L   A   R   V   S   V   E   V   I   R   D   I   R   V   K   N   R 2331              2340              2349              2358              2367              2376
GTC GTT TTT TCA GGT AAC TGT ACA AAT CTC TCT GAG GCA GCC CGG GCA AGG CTT
 V   V   F   S   G   N   C   T   N   L   S   E   A   A   R   A   R   L 2385              2394              2403              2412              2421              2430
GTA GGC CTT GCA AGT GCG TAC CAA CGC CAA GAA AAA AGA GTG GAT ATG TTA CAC
 V   G   L   A   S   A   Y   Q   R   Q   E   K   R   V   D   M   L   H
```

FIGURE 6-8

```
2439        2448        2457        2466        2475        2484
GGG GCC CTA GGG TTT TTG CTT AAA CAG TTT CAC GGC CTG TTA TTT CCT CGG GGT
 G   A   L   G   F   L   L   K   Q   F   H   G   L   L   F   P   R   G 2493        2502        2511        2520        2529        2538
ATG CCA AAC AGT AAA TCC CCC AAC CCG CAG TTT TGG ACC CTG TTA CAA
 M   P   N   S   K   S   P   N   P   Q   W   T   L   L   Q 2547        2556        2565        2574        2583        2592
CGC AAC CAG ATG CCG GCA GAT AAA CTT ACA CAC GAA GAG ATT ACC ACT ATT GCA
 R   N   Q   M   P   A   D   K   L   T   H   E   E   I   T   T   I   A 2601        2610        2619        2628        2637        2646
GCT GTT AAA CGG TTT ACC GAG GAA TAT GCA GCA ATA AAC TTT ATT AAT CTA CCC
 A   V   K   R   F   T   E   E   Y   A   A   I   N   F   I   N   L   P 2655        2664        2673        2682        2691        2700
CCA ACC TGC ATA GGA GAA TTA GCC CAG TTT TAT ATG GCA AAT CTT ATT CTT AAA
 P   T   C   I   G   E   L   A   Q   F   Y   M   A   N   L   I   L   K 2709        2718        2727        2736        2745        2754
TAC TGC GAT CAT TCA CAG TAC CTT ATA AAT ACC TTA ACT TCT ATA ATT ACG GGT
 Y   C   D   H   S   Q   Y   L   I   N   T   L   T   S   I   I   T   G
```

FIGURE 6-9

```
        2763            2772            2781            2790            2799            2808
GCC AGG CGC CCG CGT GAC CCA TCA TCC GTT TTG CAT TGG ATT CGT AAA GAT GTC
 A   R   R   P   R   D   P   S   S   V   L   H   W   I   R   K   D   V 2817            2826            2835            2844            2853            2862
ACG TCC GCC GCG GAC ATA GAA ACC CAA GCA AAG GCG CTT CTT GAA AAA ACG GAA
 T   S   A   A   D   I   E   T   Q   A   K   A   L   L   E   K   T   E 2871            2880            2889            2898            2907            2916
AAC TTA CCG GAA TTA TGG ACT ACG GCT TTT ACT CAT TCA ACT CAT TTA GTC CGC GCG
 N   L   P   E   L   W   T   T   A   F   T   S   T   H   L   V   R   A 2925            2934            2943            2952            2961            2970
GCC ATG CAA CGT CCC ATG GTC GTT TTA GGA ATA AGC ATT AGT AAA TAT CAC
 A   M   Q   R   P   M   V   V   L   G   I   S   I   S   K   Y   H 2979            2988            2997            3006            3015            3024
GGA GCG GCA GGA AAC AAC CGC GTC TTT CAG GCA GAT TGG AGC GGT TTA AAC
 G   A   A   G   N   N   R   V   F   Q   A   D   W   S   G   L   N 3033            3042            3051            3060            3069            3078
GGG GGT AAA AAT GTA TGC CCG CTA TTT ACA TTT GAT CGC ACT CGC CGT TTT ATA
 G   G   K   N   V   C   P   L   F   T   F   D   R   T   R   R   F   I 3087            3096            3105            3114            3123            3132
ATA GCA TGT CCT AGA GGA GGT TTT ATC TGC CCC GTA ACA GGT CCC TCG TCG GGA
 I   A   C   P   R   G   G   F   I   C   P   V   T   G   P   S   S   G
```

FIGURE 6-10

```
     3141            3150            3159            3168            3177          3186
AAT CGA GAA ACC ACC CTA TCC GAC CAA GTT CGC GGT ATA ATT GTC AGT GGC GGG
 N   R   E   T   T   L   S   D   Q   V   R   G   I   I   V   S   G   G 3195            3204            3213            3222            3231          3240
GCC ATG GTT CAA TTA GCC ATA TAC GCC ACG GTT GTC CGT GCA GTG GGC GCT CGA
 A   M   V   Q   L   A   I   Y   A   T   V   V   R   A   V   G   A   R 3249            3258            3267            3276            3285          3294
GCA CAA CAT ATG GCA TTT GAC GAC TGG TTA AGT CTT ACA GAC GAT GAG TTT TTA
 A   Q   H   M   A   F   D   D   W   L   S   L   T   D   D   E   F   L 3303            3312            3321            3330            3339          3348
GCC AGA GAC TTG GAG GAG TTA CAC GAC CAG ATT ATC CAA ACC CTG GAA ACG CCC
 A   R   D   L   E   E   L   H   D   Q   I   I   Q   T   L   E   T   P 3357            3366            3375            3384            3393          3402
TGG ACC GTA GAA GGC GCT CTA GAA GCA GTA AAG ATT CTA GAT GAA AAA ACG ACA
 W   T   V   E   G   A   L   E   A   V   K   I   L   D   E   K   T   T 3411            3420            3429            3438            3447          3456
GCG GGA GAT GGG GAA ACC CCC ACA AAC CTA GCA TTT AAT TTT GAT TCT TGT GAA
 A   G   D   G   E   T   P   T   N   L   A   F   N   F   D   S   C   E
```

FIGURE 6-11

```
         3465              3474              3483              3492              3501              3510
CCA AGC CAT GAC ACC ACA TCT AAC GTA TTA AAC ATT TCA GGG TCA AAC ATT TCA
 P   S   H   D   T   T   S   N   V   L   N   I   S   G   S   N   I   S 3519              3528              3537              3546              3555              3564
GGG TCA ACT GTC CCT GGT CTT AAA CGA CCC CCC GAA GAT GAC GAA CTC TTT GAT
 G   S   T   V   P   G   L   K   R   P   P   E   D   D   E   L   F   D 3573              3582              3591              3600              3609
CTT AGT GGT ATT CCC ATA AAA CAT GGG AAC ATT ACA ATG GAA ATG A 3'
 L   S   G   I   P   I   K   H   G   N   I   T   M   E   M
```

VZV ORF29P PROTEIN-RELATED COMPOSITIONS AND METHODS

This application claims the benefit of copending U.S. Provisional Application No. 60/177,901, filed Jan. 25, 2000, the contents of which are hereby incorporated by reference.

The invention described herein was made with Government support under grant numbers AI-01409 and AI-124021 from the National Institutes of Health. Accordingly, the United States Government has certain rights in this invention.

BACKGROUND OF THE INVENTION

Throughout this application, various publications are referenced by arabic numbers within parentheses. Disclosures of these publications in their entirety are hereby incorporated by reference into this application to more fully describe the state of the art to which this invention pertains.

Varicella-Zoster Virus ("VZV") infects dorsal root ganglia ("DRG"), enters latency, and may later reactivate to cause zoster. Studies have detected VZV in specific sites at different stages of infection. VZV DNA is present in the oropharynx (27) and in peripheral blood mononuclear cells ("PBMCs") of patients with chickenpox (3, 16, 20). Virus DNA, the glycoproteins gE and gB, and the immediate-early protein 63 ("IE63p") are found in skin biopsy samples obtained from patients with chickenpox or zoster (1, 23–25). VZV is found in keratinocytes, antigen-presenting cells, and endothelial cells during acute zoster (23, 25) and in keratinocytes and inflammatory cells during chickenpox (1). VZV is present in neurons and satellite cells of DRG years following primary infection (6–8, 12, 17, 22) and has been observed by electron microscopy in sensory nerves during zoster (10). Other details of VZV pathogenesis remain speculative, including how the virus spreads from respiratory epithelial cells to PBMCs, keratinocytes, and DRG. Because PBMCs, sensory nerves, and epithelial cells are in close proximity in the dermis and epidermis, the skin is likely the site where this virus enters the nervous system.

By analogy with herpes simplex virus ("HSV"), it is thought that VZV transcription is temporally regulated. Immediate-early ("IE") genes are expressed first, followed by early ("E") genes and lastly late ("L") genes (5). Some VZV proteins encoded by IE and L genes are incorporated in the virion, including trans-activators such as IE63p and structural proteins such as gC (14, 15). ORF29p (for open reading frame 29 protein), the major VZV DNA-binding protein, is encoded by a putative E gene and is not detected in purified virions (13). ORF29p is also referred to herein as "29p protein", "ORF29p protein", and "VZV ORF29p protein." During latency, VZV exhibits limited gene expression (6–9, 22), with the accumulation of specific IE and E gene-encoded proteins in neurons (18, 19). During reactivation, all kinetic classes of VZV genes are expressed in neurons (18). Whether VZV is in the lytic or latent state is reflected by the localization of expressed VZV gene products. VZV IE and E proteins that are present in both the nucleus and cytoplasm during productive infection are detected only in the cytoplasm of neurons during latency (18).

Early observations suggested that there were inclusion bodies in endothelial cells present in varicella lesions (29). However, there was no known association between VZV histology and viral etiology at that time.

SUMMARY OF THE INVENTION

The present invention provides a first composition of matter comprising 29p protein having bound thereto an agent whose delivery into a eukaryotic cell is desired, which composition of matter enters the cell upon contact therewith.

The present invention also provides a second composition of matter comprising a 29p protein having operably affixed thereto a lipid-soluble moiety which permits the protein to be anchored to a lipid membrane.

The present invention also provides a lipid vesicle comprising the second composition of matter anchored thereto via its lipid-soluble moiety, such that the 29p protein is situated on the vesicle's outer surface and facilitates delivery of the vesicle's contents into a eukaryotic cell when the vesicle is contacted therewith. The present invention further provides a monoclonal antibody which specifically binds to 29p protein.

The present invention further provides a method for delivering an agent into a eukaryotic cell comprising contacting the agent with the cell, wherein the agent has bound thereto 29p protein which enters the cell upon contact therewith, thereby delivering the agent into the cell.

The present invention further provides a method for causing a eukaryotic cell to secrete a desired protein in the form of a fusion protein, comprising introducing into the cell a vector for expressing a fusion protein that comprises the desired protein and 29p protein operably affixed thereto, whereby the cell expresses the fusion protein and the 29p protein thereof permits the fusion protein's exit from the cell, thereby causing the cell to secrete the desired protein in the form of a fusion protein.

The present invention further provides a pharmaceutical composition comprising (a) a composition of matter comprising 29p protein having bound thereto a therapeutic or prophylactic agent, which composition of matter enters a eukaryotic cell upon contact therewith, and (b) a pharmaceutically acceptable carrier.

The present invention further provides a pharmaceutical composition comprising a pharmaceutically acceptable carrier, and a lipid vesicle comprising (a) a therapeutic or prophylactic agent therein, and (b) a 29p protein having operably affixed thereto a lipid-soluble moiety, which protein (i) is anchored to the vesicle via its lipid-soluble moiety, (ii) is situated on the vesicle's outer surface, and (iii) facilitates delivery of the agent into a eukaryotic cell when the vesicle is contacted therewith.

The present invention further provides a method for treating a subject afflicted with a disorder comprising administering to the subject a therapeutically effective amount of the first or second pharmaceutical composition, wherein the therapeutic agent therein is known to ameliorate the disorder.

The present invention further provides a method for inhibiting the onset of a disorder in a subject comprising administering to the subject a prophylactically effective amount of the first or second pharmaceutical composition, wherein the prophylactic agent therein is known to inhibit the disorder's onset.

The present invention further provides a nucleic acid molecule which hybridizes to at least a portion of a nucleic acid molecule encoding 29p protein.

The present invention further provides a method for detecting the presence of a 29p protein-encoding nucleic acid molecule in a sample comprising the steps of (a) contacting the sample with the instant detectable nucleic acid molecule under conditions permitting it to hybridize to a 29p protein-encoding nucleic acid molecule if present in the sample, and (b) detecting the presence of any detectable nucleic acid molecule so hybridized, thereby detecting the presence of a 29p protein-encoding nucleic acid molecule in the sample.

Finally, the present invention provides a method for quantitatively determining the amount of 29p protein-encoding nucleic acid molecule in a sample comprising the steps of (a) contacting the sample with the instant detectable nucleic acid molecule under conditions permitting it to hybridize to any 29p protein-encoding nucleic acid molecule present in the sample, (b) quantitatively determining the amount of detectable nucleic acid molecule so hybridized, and (c) comparing this amount to a known standard, thereby quantitatively determining the amount of 29p protein in the sample.

BRIEF DESCRIPTION OF THE FIGURES

FIG. 6. Protein and nucleotide sequences. ORF29p amino acid sequence and nucleotide sequence encoding it.

DETAILED DESCRIPTION OF THE INVENTION

Figure 1A:
FIG. 1. Immunohistochemical detection of ORF29p in skin biopsy samples. Chickenpox (A), zoster (B), and Grover's disease (C) skin lesions were analyzed for ORF29p as previously described (18), with the following exceptions. All washes were performed in Tris-buffered saline, and the signal was developed for 10 min in AP substrate (Vector Laboratories, Inc., Burlingame, Calif.), according to the manufacturer's recommendations, in the presence of levamisole to inhibit endogenous alkaline phosphatase activity. Arrows indicate positive epithelial cells. Magnification, ×100.
Figure 1B:
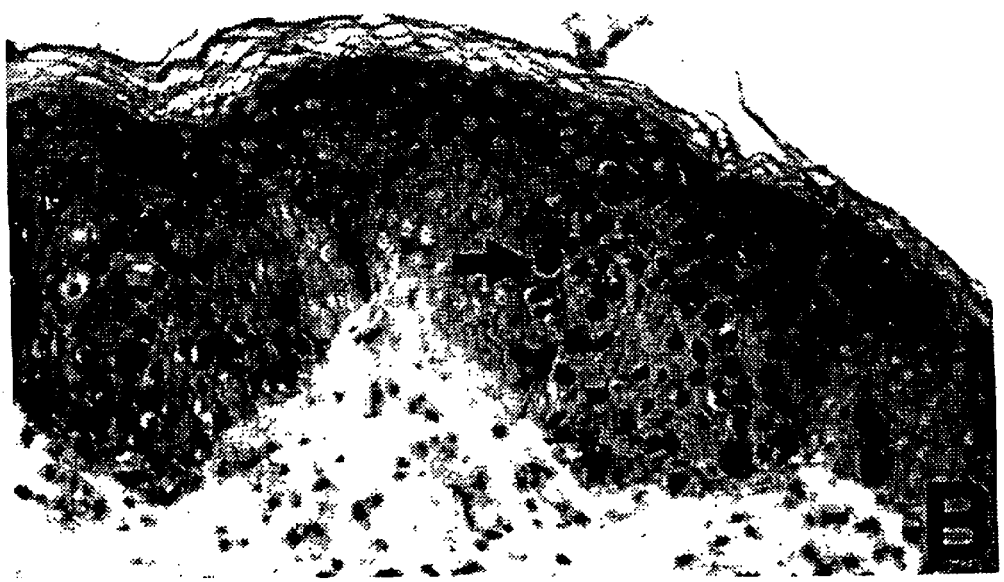
Figure 1C:
Figure 2A:
FIG. 2. Immunohistochemical detection of ORF29p and CD43 in skin biopsy samples. Skin biopsy samples from a patient with chickenpox (A and B) or a patient with zoster (C and D) were probed for the presence of ORF29p (A and C) or ORF29p and CD43 (B and D) as described in the legend to FIG. 1. Gray arrows indicate endothelial cells containing ORF29p. Black arrows indicate cells expressing CD43 that contain ORF29p. Magnification, ×600.
Figure 2B:
Figure 2C:
Figure 2D:
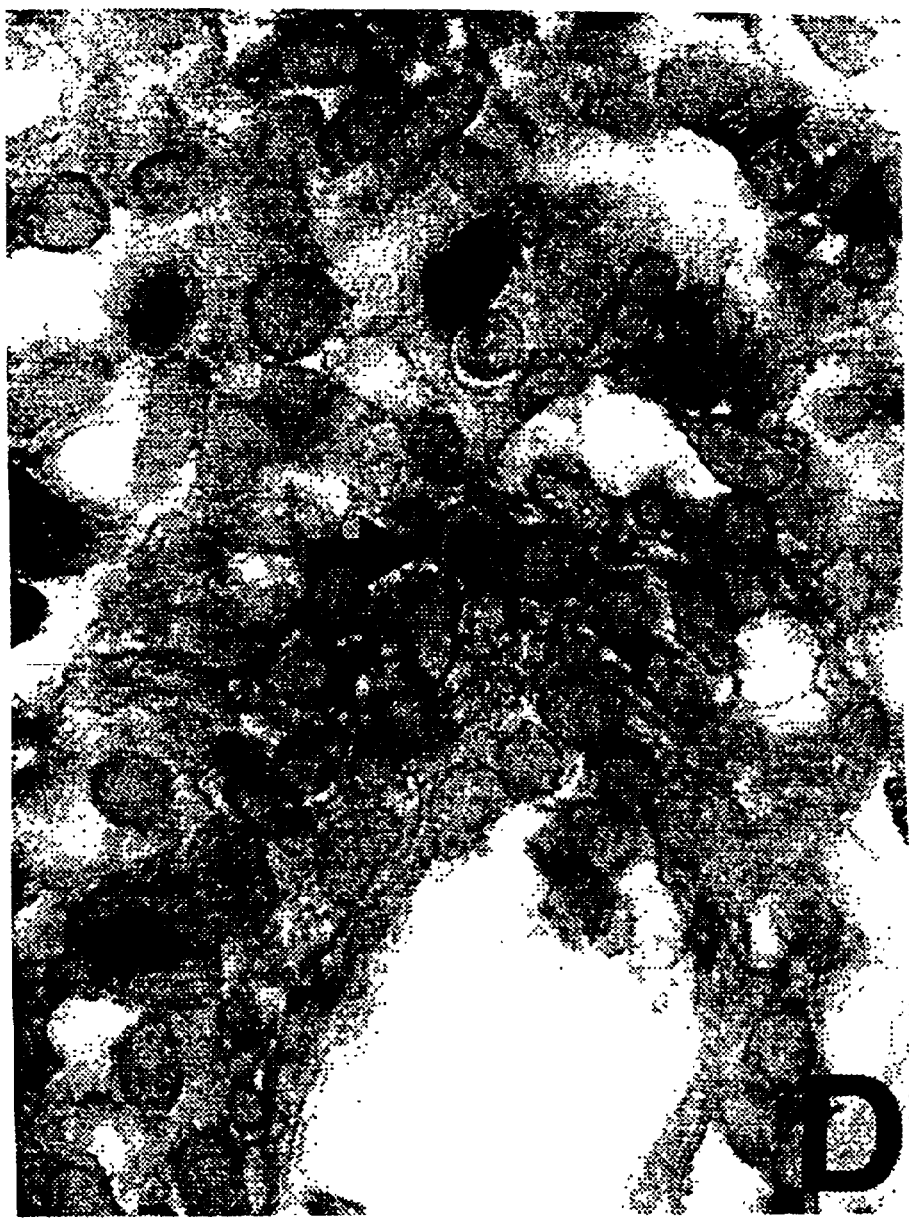
Figure 3A:
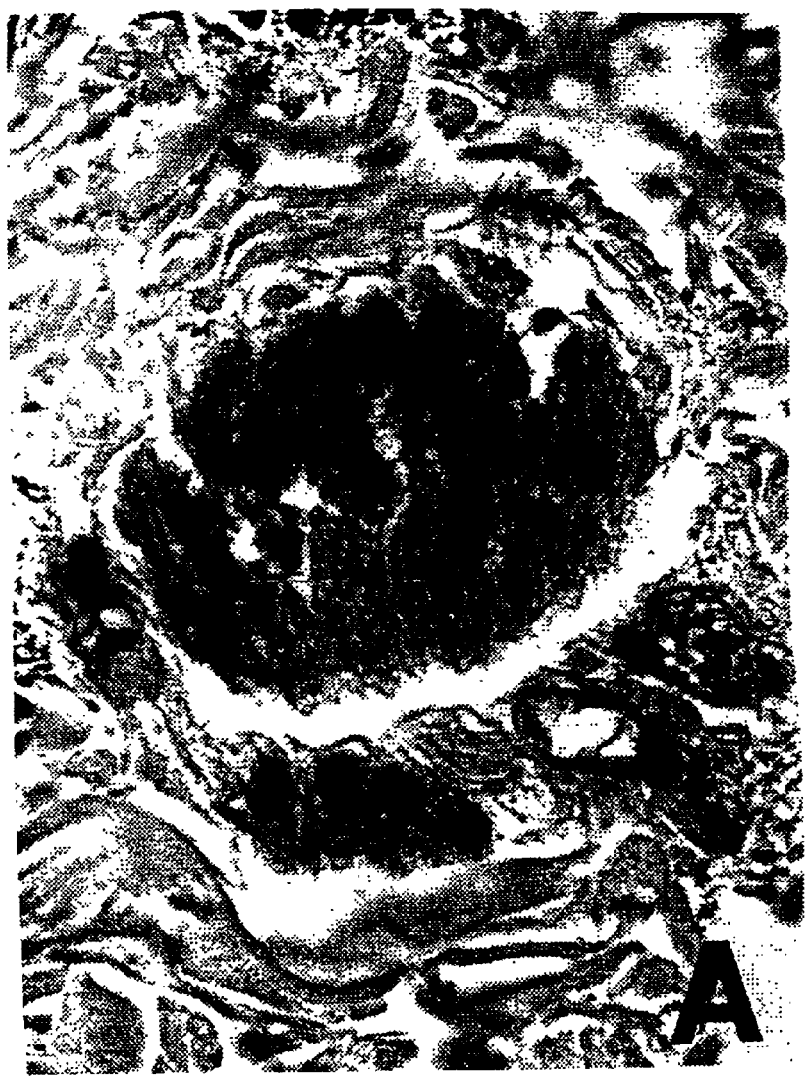
FIG. 3. Immunohistochemical detection of ORF29D and gC in skin biopsy samples. Sections of nerves in the dermis underlying chickenpox (A and B) or zoster (C and D) lesions underwent immunohistochemistry for ORF29p (A and C) or gC (B and D) as described in the legend to FIG. 1. Magnification, ×400.
Figure 3B:
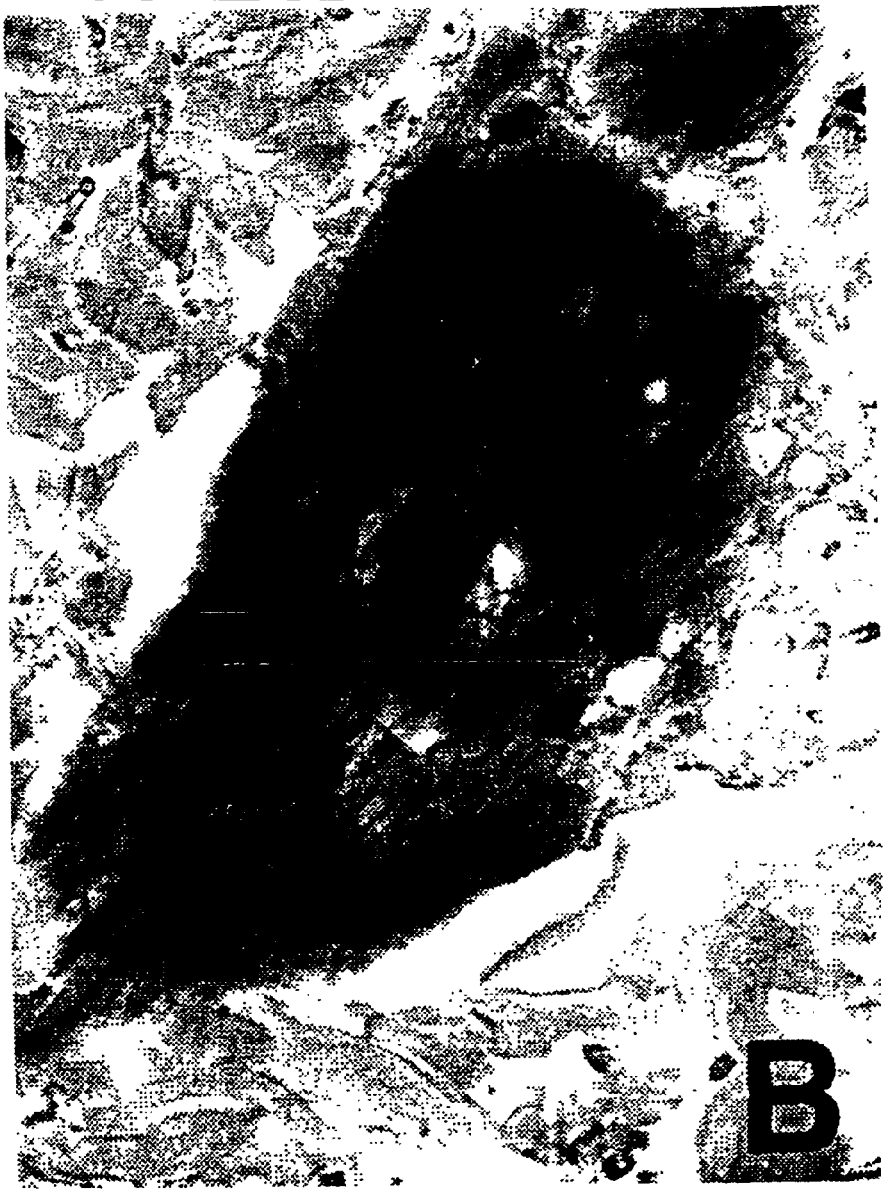
Figure 3C:
Figure 3D:

This invention is based on the surprising discovery that the Varicella-Zoster Virus protein ORF29p can readily enter and exit eukaryotic cells. This unusual property renders it advantageous as, among other things, a vehicle for delivering agents to, and secreting them from, eukaryotic cells.

Specifically, the present invention provides a first composition of matter comprising 29p protein having bound thereto an agent whose delivery into a eukaryotic cell is desired, which composition of matter enters the cell upon contact therewith.

As used herein, the term "29p protein" shall mean the protein having the sequence identified in FIG. 6 or a naturally-occurring variant thereof. As stated above, "29p protein" is alternatively referred to herein as "ORF29p", "ORF29p protein", and "VZV ORF29p protein."

The agent of the first composition can be of any physical category. In one embodiment, the agent is a protein or a peptide. In another embodiment, the agent is a nucleic acid molecule. In a further embodiment, the agent is an organic compound.

An agent that is a "protein" is a polypeptide sequence greater than 10 amino acids in length. An agent that is a "peptide" is a polypeptide having a sequence less than or equal to 10 amino acids in length. Examples of protein agents include, for example, insulin, factors VIII and IX, proteases, alpha-glucosidase, glucocerebrosidase, adenosine deaminase, and DNAase.

An agent that is a "nucleic acid molecule" can be any nucleic acid molecule, including, without limitation, DNA (e.g., cDNA and genomic DNA), RNA (e.g., mRNA and rRNA), and hybrids thereof. The nucleic acid bases that form nucleic acid molecules can be the bases A, C, G, T, and U, as well as derivatives thereof. Derivatives of these bases are well known in the art, and are exemplified in PCR Systems, Reagents and Consumables (Perkin Elmer Catalogue 1996–1997, Roche Molecular Systems, Inc., Branchburg, N.J., USA). "Nucleic acid molecules" further include, without limitation, antisense, expression vectors, and catalytic nucleic acids such as ribozymes and DNAzymes.

Organic compounds include, without limitation, nutrients such as vitamins, and organic pharmaceuticals such as analgesics, anesthetics, anticonvulsants, antidiabetic agents, anti-infective agents, antineoplastics, gastrointestinal agents, immunosuppressives, parasympatholytics, and parasympathomimetics. Other organic compounds are well known in the art (see, e.g., Physician's Desk Reference, 53rd ed., 1999).

In the first composition of matter, the agent can be "bound" to the 29p protein either covalently or non-covalently. Examples of covalent binding include, without limitation, N-terminal and/or C-terminal fusion proteins in the case of protein or peptide agents, and peptide or other chemical linkages in the case of agents that are nucleic acids or organic molecules. Methods of forming covalent bonds between proteins, proteins and nucleic acid molecules, and proteins and organic molecules are routine in the art. In addition the agent can be bound to the 29p protein non-covalently. Examples of non-covalent bonds include, for example, those between 29p protein and an antibody directed thereto.

Delivery of the agent into a cell can be for any purpose, e.g., therapeutic, prophylactic, diagnostic, and labeling. As used herein, an entity is "delivered" into a eukaryotic cell if it traverses the cell membrane and enters the cytoplasm, nucleus, or other organelle thereof. Mechanisms of entry include, without limitation, cellular endocytosis.

The eukaryotic cell into which the instant composition is delivered can be any eukaryotic cell. In the preferred embodiment, the eukaryotic cell is a mammalian cell, e.g., a murine or human cell. Eukaryotic cells include, without limitation, Hela cells, fibroblasts, astrocytes, neurons, NB41 cells, and SupT-1 cells. Conditions under which the instant composition of matter will enter a eukaryotic cell include, for example, physiological conditions.

The present invention also provides a second composition of matter comprising a 29p protein having operably affixed thereto a lipid-soluble moiety which permits the protein to be anchored to a lipid membrane.

The present invention further provides a lipid vesicle comprising the second composition of matter anchored thereto via its lipid-soluble moiety, such that the 29p protein is situated on the vesicle's outer surface and facilitates delivery of the vesicle's contents into a eukaryotic cell when the vesicle is contacted therewith. In the preferred embodiment, the vesicle's contents comprise an agent whose delivery into a cell is desired.

As used herein, the term "lipid-soluble moiety" shall mean an entity such as a hydrophobic polypeptide chain or a phospholipid capable of integrating within a lipid bilayer membrane. In one embodiment, the lipid-soluble moiety comprises a polypeptide chain bound to the N- or C-terminus of the 29p protein. Such fusion proteins can be made using known methods. The lipid-soluble moiety is "operably affixed" to the 29p protein if it does not interfere with the 29p protein's ability to enter a eukaryotic cell when contacted therewith. The second composition of matter is "anchored to a lipid membrane" in that it is immobilized with respect to the lipid membrane due to the lipid-soluble moiety's integration therein. Finally, as used herein, a vesicle's "contents" shall mean everything in or on the vesicle except the vesicle membrane and 29p protein anchored thereto.

The present invention also provides a monoclonal antibody which specifically binds to 29p protein. In one embodiment, the monoclonal antibody is labeled with a detectable marker. As used herein, the term "antibody" includes, without limitation, murine, human and humanized antibodies, and antigen-binding fragments thereof. Methods of generating monoclonal antibodies are wellknown (30).

The present invention further provides a method for delivering an agent into a eukaryotic cell comprising contacting the agent with the cell, wherein the agent has bound thereto 29p protein which enters the cell upon contact therewith, thereby delivering the agent into the cell.

The present invention further provides a method for causing a eukaryotic cell to secrete a desired protein in the form of a fusion protein, comprising introducing into the cell a vector for expressing a fusion protein that comprises the desired protein and 29p protein operably affixed thereto, whereby the cell expresses the fusion protein and the 29p protein thereof permits the fusion protein's exit from the cell, thereby causing the cell to secrete the desired protein in the form of a fusion protein. As used herein, the "secretion" of a protein by a cell shall mean the exit of that protein from the cell by any means. Expression vectors useful for carrying out the instant method are well known in the art (30).

As used herein, the term "fusion protein" shall mean a protein having a plurality of regions, each corresponding to a distinct protein or fragment thereof. Fusion proteins can include linker regions connecting the regions thereof, which are known in the art.

The present invention further provides a first pharmaceutical composition comprising (a) a composition of matter comprising 29p protein having bound thereto a therapeutic or prophylactic agent, which composition of matter enters a eukaryotic cell upon contact therewith, and (b) a pharmaceutically acceptable carrier.

The present invention further provides a second pharmaceutical composition comprising a pharmaceutically acceptable carrier, and a lipid vesicle comprising (a) a therapeutic or prophylactic agent therein, and (b) a 29p protein having operably affixed thereto a lipid-soluble moiety, which protein (i) is anchored to the vesicle via its lipid-soluble moiety, (ii) is situated on the vesicle's outer surface, and (iii) facilitates delivery of the agent into a eukaryotic cell when the vesicle is contacted therewith.

The present invention further provides a method for treating a subject afflicted with a disorder comprising administering to the subject a therapeutically effective amount of the first or second pharmaceutical composition, wherein the therapeutic agent therein is known to ameliorate the disorder.

The present invention further provides a method for inhibiting the onset of a disorder in a subject comprising administering to the subject a prophylactically effective amount of the first or second pharmaceutical composition, wherein the prophylactic agent therein is known to inhibit the disorder's onset.

As used herein, "subject" shall mean any animal, such as a primate, mouse, rat, guinea pig, or rabbit. In the preferred embodiment, the subject is a human.

As used herein, "inhibiting the onset of a disorder" shall mean either lessening the likelihood of the disorder's onset, or preventing the onset of the disorder entirely. In the preferred emmbodiment, inhibiting the onset of a disorder means preventing its onset entirely.

As used herein, "treating" a disorder shall mean slowing, stopping, or reversing the disorder's progression. In the preferred embodiment, "treating" a disorder means reversing the disorder's progression, ideally to the point of eliminating the disorder itself. As used herein "ameliorating" and "treating" a disorder are equivalent.

Determining a therapeutically effective or prophylactically effective amount of the pharmaceutical composition can be done based on animal data using routine computational methods. In one embodiment, the therapeutically or prophylactically effective amount is an amount sufficient to deliver to the subject between about 1 $\mu$g/kg and 1 g/kg of the 29p protein therein. In another embodiment, the effective amount is an amount sufficient to deliver to the subject between about 100 $\mu$g/kg and 100 mg/kg of the 29p protein therein. In another embodiment, the effective amount is an amount sufficient to deliver to the subject between about 1 mg/kg and 10 mg/kg of the 29p protein therein. In another embodiment, the effective amount is an amount sufficient to deliver to the subject between about 10 mg/kg and 100 mg/kg of the 29p protein therein.

In the present invention, administering the instant pharmaceutical compositions can be effected or performed using any of the various methods and delivery systems known to those skilled in the art. The administering can be performed, for example, intravenously, orally, via implant, transmucosally, transdermally, intramuscularly, and subcutaneously. The pharmaceutical carriers used in the instant pharmaceutical compositions are well known to those skilled in the art. The following drug delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g. ethanol, propylene glycol and sucrose) and polymers (e.g. polycaprylactones, and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems are preferred, and include, for example, aqueous and nonaqueous gels, creams, multiple emulsions, microemulsions, liposomes, ointments, aqueous and nonaqueous solutions, lotions aerosols, hydrocarbon bases and powders, and can contain excipients such as solubilizers, permeation enhancers, (e.g. fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid $N,N^I,N^{II},N^{III}$-tetramethyl-$N,N^I,N^{II}$, $N^{III}$-tetrapalmityl-spermine and dioleoyl phosphatidyl ethanolamine (DOPE)(GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N, N-trimethylammonium methylsulfate)(Boehringer Manheim); and (4) Lipofectamine, 3:1 (M/M) liposome formulation of the polycationic lipid DOSPA and the neutral lipid DOPE (GIBCO BRL). Herein, the term "liposome" and "lipid vesicle" are used interchangebly. In the instant pharmaceutical compositions comprising 29p protein-containing lipid vesicles, the term "pharmaceutically acceptable carrier" refers to carriers other than liposomes.

Solutions, suspensions and powders for reconstitutable delivery systems include vehicles such as suspending agents (e.g., gums, zanthans, cellulosics and sugars), humectants (e.g. sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

The present invention further provides a nucleic acid molecule which hybridizes to at least a portion of a nucleic acid molecule encoding 29p protein.

In one embodiment, the nucleic acid molecule encoding 29p protein has the sequence shown in FIG. 6. In a further embodiment, the nucleic acid molecule is complementary to the nucleic acid molecule having the sequence shown in FIG. 6.

The invention further provides the nucleic acid molecule which hybridizes to at least a portion of a nucleic acid molecule encoding 29p protein, wherein the nucleic acid molecule is labeled with a detectable marker.

The present invention further provides a method for detecting the presence of a 29p protein-encoding nucleic acid molecule in a sample comprising the steps of (a) contacting the sample with the instant detectable nucleic acid molecule under conditions permitting it to hybridize to a 29p protein-encoding nucleic acid molecule if present in the sample, and (b) detecting the presence of any detectable nucleic acid molecule so hybridized, thereby detecting the presence of a 29p protein-encoding nucleic acid molecule in the sample.

Finally, the present invention provides a method for quantitatively determining the amount of 29p protein-encoding nucleic acid molecule in a sample comprising the steps of (a) contacting the sample with the instant detectable nucleic acid molecule under conditions permitting it to hybridize to any 29p protein-encoding nucleic acid molecule present in the sample, (b) quantitatively determining the amount of detectable nucleic acid molecule so hybridized, and (c) comparing this amount to a known standard, thereby quantitatively determining the amount of 29p protein in the sample.

Conditions permitting nucleic acid hybridization are well known in the art and include, without limitation, physiological conditions (30). Detectable markers are known in the art, and include, without limitation, markers utilizing fluorescence and radiolabeling.

The known standard to which the amount of hybridized detectable nucleic acid molecule is compared can be, for example, one or more data points correlating known amounts of 29p protein-encoding nucleic acid molecule with the amounts of detectable nucleic acid molecule that hybridize therewith.

The definitions of terms set forth in the Detailed Description of the Invention are applicable wherever such terms occur herein, unless stated otherwise.

The present invention is illustrated in the Experimental Details section which follows. This section is set forth to aid in an understanding of the invention but is not intended to, and should not be construed to, limit in any way the invention as set forth in the claims which follow thereafter.

Experimental Details

The ORF29p protein is a 131 kdalton protein encoded by a 3612 bp open reading frame in the varicella zoster virus (VZV). On the basis of nucleotide and amino acid homology the protein was predicted to be a homologue of ICP8, a well characterized single-stranded DNA-binding protein from herpes simplex virus (HSV). Subsequent biochemical studies have verified this to be the case VZV and HSV are members of the family alphaherpesviridae.

We demonstrated that ORF29p was detected in peripheral nerves in the dermis in biopsy specimens taken from patients with chicken pox. Because of the role of this protein in the replication of virus DNA, which occurs in the nucleus of infected cells, this was an unexpected finding. When medium from cells infected with HSV or VZV was harvested, clarified by centrifugation and subsequently filtered to remove cells and large debris we were able to demonstrate that ORF29p, but not ICP8, was secreted from tissue culture cells infected in vitro, in vivo, and ex vivo. The clarified supernatants from cells infected with VZV but not HSV contained a protein with the mobility characteristic of ORF29p that reacted with antibody specific for this protein.

Subsequent assays of the filtered tissue culture medium from VZV infected cells demonstrated that the ORF29p protein present in the medium was able to enter cultivated human neurons as evidenced by immunohistochemical analysis. In similar, but unpublished, studies we have demonstrated that ORF29p is assimilated by human lymphocytes. In other unpublished studies, we have shown that recombinant ORF29p, purified from insect cells infected with a baculovirus expressing the protein, is taken up by cultured human neurons and detected in both the cytoplasm and nucleus of these cells.

Thus, ORF29p has the potential to be used as a charon for the delivery of pharmaceuticals to a wide spectrum of human cells. For example, delivery of analgesics coupled to ORF29p to sensory nerves in areas of the body where there is intense local pain could provide local relief. These pharmaceuticals could include biological macromolecules and small molecules such as hormones, growth factors, enzymes, toxins, antiviral agents and chemical compounds to be used as drugs.

EXAMPLE 1

Varicella-Zoster Virus Proteins in Skin Lesions: Implications for a Novel Role of ORF29p in Chickenpox Skin biopsy samples from varicella-zoster virus (vzv)-infected patients examined by immunohistochemistry demonstrated VZV replication in nonepithelial cell types. ORF29p, a nonstructural nuclear protein, was found in nerves of two of six patients with chickenpox. In tissue culture, ORF29p was secreted by VZV-infected fibroblasts. Extracellular ORF29p can be taken up through endocytosis by human neurons, implying a novel role for this protein in pathogenesis.

To determine if, during primary infection, as in zoster, VZV infects endothelial cells and nerves in the dermis and to characterize the inflammatory cells in the epidermis and dermis infected by VZV, we performed comparative immunohistochemical analyses of skin biopsy samples obtained from patients with chickenpox and zoster.

Comparative immunohistochemical analysis of chickenpox and zoster lesions. Six cases of chickenpox and eight cases of zoster were analyzed by immunohistochemistry using purified polyclonal antibodies generated against VZV proteins (18). Each specimen was analyzed for the presence of gC, a late gene product and component of the virus envelope (15); IE63p, a regulatory protein and component of the virus tegument (14); and ORF29p (13). In these specimens, antibodies to IE63p, ORF29p, and gC detected proteins in the expected intracellular compartments: ORF29p was found in cell nuclei (FIG. 1), gC was found in cell membranes and the cytoplasm, and IE63p was found in both the cell nucleus and cytoplasm (data not shown). VZV proteins were detected in epithelial cells, endothelial cells, nerves, and CD43+/CD68+ inflammatory cells in the epidermis and dermis in both chickenpox and zoster cases (FIG. 1 and 2). Among the six chickenpox specimens, all were positive for ORF29p, four were positive for IE63p, and five were positive for gC. Among the eight zoster specimens, all were positive for ORF29p, five were positive for IE63p, and five were positive for gC (Table 1).

TABLE 1

Detection of VZV proteins in skin biopsy samples[a]

| Diagnosis | No. positive/no. examined | VZV protein[b] IE63p EP | IE63p EN | IE63p NE | ORF29p EP | ORF29p EN | ORF29p NE | ORF29p WBC[c] | gC EP | gC EN | gC NE |
|---|---|---|---|---|---|---|---|---|---|---|---|
| CP | 6/6 | 4 | 3 | 0 | 6 | 4 | 2 | 4 | 4 | 5 | 3 |
| Z | 8/8 | 5 | 1 | 0 | 8 | 4 | 0 | 5 | 5 | 5 | 4 |
| G | 0/5 | 0 | 0 | 0 | 0 | 0 | 0 | 0 | 0 | 0 | 0 |
| HSV-2 | 0/3 | 0 | 0 | 0 | 0 | 0 | 0 | 0 | 0 | 0 | 0 |

[a]Tissues from patients with clinical and histopathological diagnoses of chickenpox (CP), zoster (Z), Grover's disease (G) or HSV-2 were subjected to immunohistochemical analysis for immediate-early (IE63p), early (ORF29p), and late (gC) virus proteins in epithelial (EP), endothelial (EN), or inflammatory cells expressing CD43 (WBC) or in dermal nerves (NE).
[b]Results are expressed as the absolute number of biopsy samples with detectable protein. Zero indicates the absence of detectable protein. [c]VZV-infected WBC from two chickenpox cases and two zoster cases were found to express CD68 and not CD3 or CD20.

These results are consistent with our experience concerning the affinities of these antibodies for their target proteins. Five cases of Grover's disease, a noninfectious dermatosis, and three cases of HSV infection were included as controls and were negative (Table 1), confirming that each antibody signal was specific. Detection of ORF29p, a DNA-binding protein not present in the virion (13), in the nuclei of infected cells demonstrates that VZV replication occurs in endothelial cells, epithelial cells, and cells of the monocyte/macrophage lineage expressing surface CD43 and CD68. Although VZV genomes were detected in circulating lymphocytes of patients with chickenpox and zoster (16, 20) we detected VZV proteins only in CD43+/CD68+ cells and not in cells expressing CD3 or CD20 in these specimens.

No differences in immunohistochemical staining were appreciated between specimens of chickenpox and zoster except for the presence of ORF29p in peripheral nerves in the dermis in two of the chickenpox specimens. ORF29p was detected in the Schwann cells and axons of nerves in these two cases (FIG. 3A), which included a biopsy sample that was obtained 2 days following the onset of the rash. Cytoplasmic localization of ORF29p is not consistent with the presence of replicating VZV or of formed virions. In contrast, ORF29p was not detected in axons or Schwann cells in the seven zoster biopsy samples with peripheral nerves apparent in the analyzed sections (FIG. 3C). The absence of ORF29p from axons during zoster was not surprising, as this protein localizes to the nucleus of productively infected cells, including neurons containing reactivating virus (18), and is not detected in virions (13). As expected, gC was found in both axons and Schwann cells of nerves in three chickenpox cases and four zoster cases (FIGS. 3B and D). Detection of gC indicates the presence of virions or replicating VZV at these sites. The significance of infection of Schwann cells in chickenpox and zoster is unclear. Schwann cells cultivated in tissue culture are permissive for VZV infection (4), but the role of these cells in pathogenesis is not known.

Secretion of ORF29p by infected cells in tissue culture. Clinical and laboratory evidence suggests that DRG are infected via the peripheral nerves during the exanthem of chickenpox (11, 21, 26). Although hematogenous and axonal spread of virus are not mutually exclusive, given the small numbers of VZV-infected circulating PBMCs (16, 20), it seems unlikely that a substantial number of neurons are infected without amplification in the epidermis and dermis. Nonetheless, the exact mechanism by which VZV reaches DRG remains unsettled.

Entry of virus particles into peripheral axons during chickenpox cannot account for the presence of ORF29p at this site because this protein is not a component of the virion (13). Assuming that the virus spreads from the skin to the peripheral nerves during the exanthem, the appearance of ORF29p in the nerve within 2 days of rash onset is surprising because of the distance between the peripheral axon and the sensory neuron in the DRG. By analogy with HSV, it is thought that VZV entering the axon in the epidermis travels by retrograde axonal transport (2) at a rate of 200 to 400 mm/day (28). Additional time would be required for VZV proteins to be produced in the neuron in the DRG and then to travel to the dermis and epidermis by anterograde axonal transport. If the DRG were infected during viremia prior to the onset of the rash, virus replication in the neuron and anterograde axonal transport of VZV proteins could occur. However, this would not explain the presence of ORF29p in peripheral axons, because ORF29p localizes to the nucleus rather than to the cytoplasm during productive infection (18). Moreover, ORF29p was not found in peripheral axons during zoster.

Figure 4:
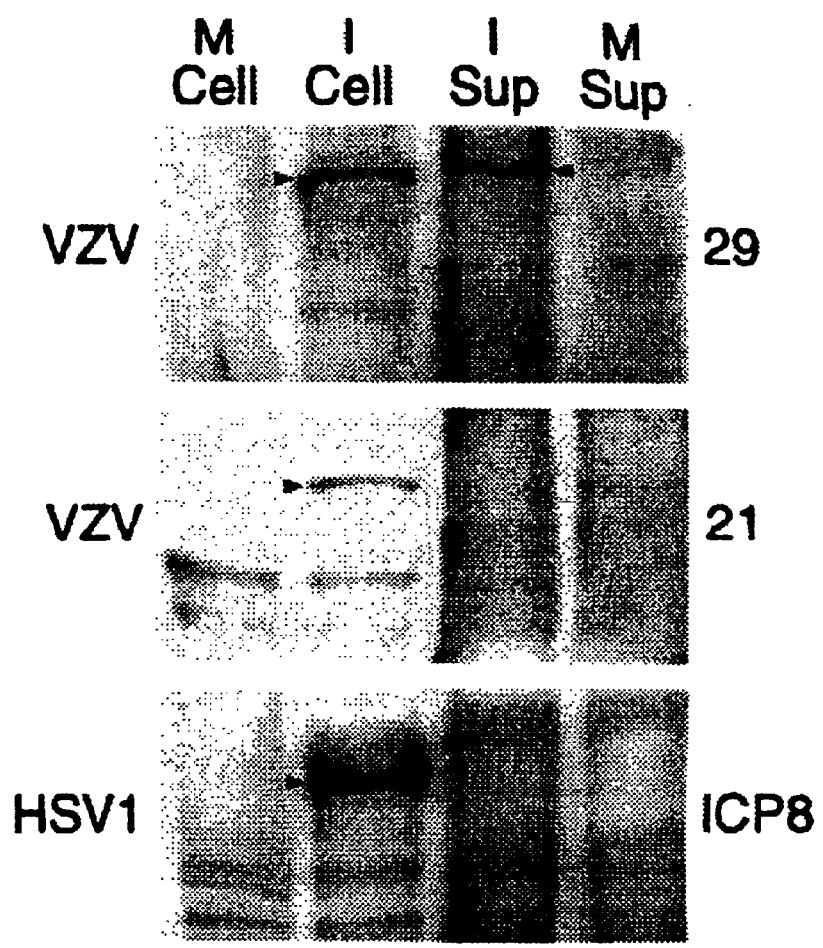
FIG. 4. Western blot analyses of VZV and HSV-1 proteins. ORF29p, ORF21p, and ICP8 were detected in mock-infected cell extracts (M Cell) and supernatants (M Sup) or cell extracts (I Cell) and supernatants (I Sup) infected with the viruses denoted on the left. The proteins were immunoprecipitated and detected using the antibodies denoted on the right. Arrowheads denote the proteins of interest.

We therefore postulated that ORF29p may be secreted by VZV-infected cells in the dermis or epidermis and enter peripheral axons by endocytosis. In order to test whether ORF29p was secreted by VZV-infected cells, tissue culture media from uninfected human embryonic lung fibroblasts (HELF) or HELF infected with VZV or HSV-1 was clarified by centrifugation and filtration to remove detached cells. Immunoprecipitation with antibodies to ORF29p, ORF21p (a putative VZV accessory DNA binding protein), or ICP8 (the HSV-1 homologue of ORF29p) was performed and the precipitated proteins were analyzed by sodium dodecyl sulfate-polyacrylamide gel electrophoresis and Western blotting. ORF29p was detected in culture supernatants of infected cells but not in culture supernatants of uninfected cells (FIG. 4). ORF21p was not detected in supernatants of VZV-infected cells, and ICP8 was not detected in supernatants of HSV-1-infected cells. Thus, ORF29p is secreted by infected fibroblasts in tissue culture.

Figure 5A:
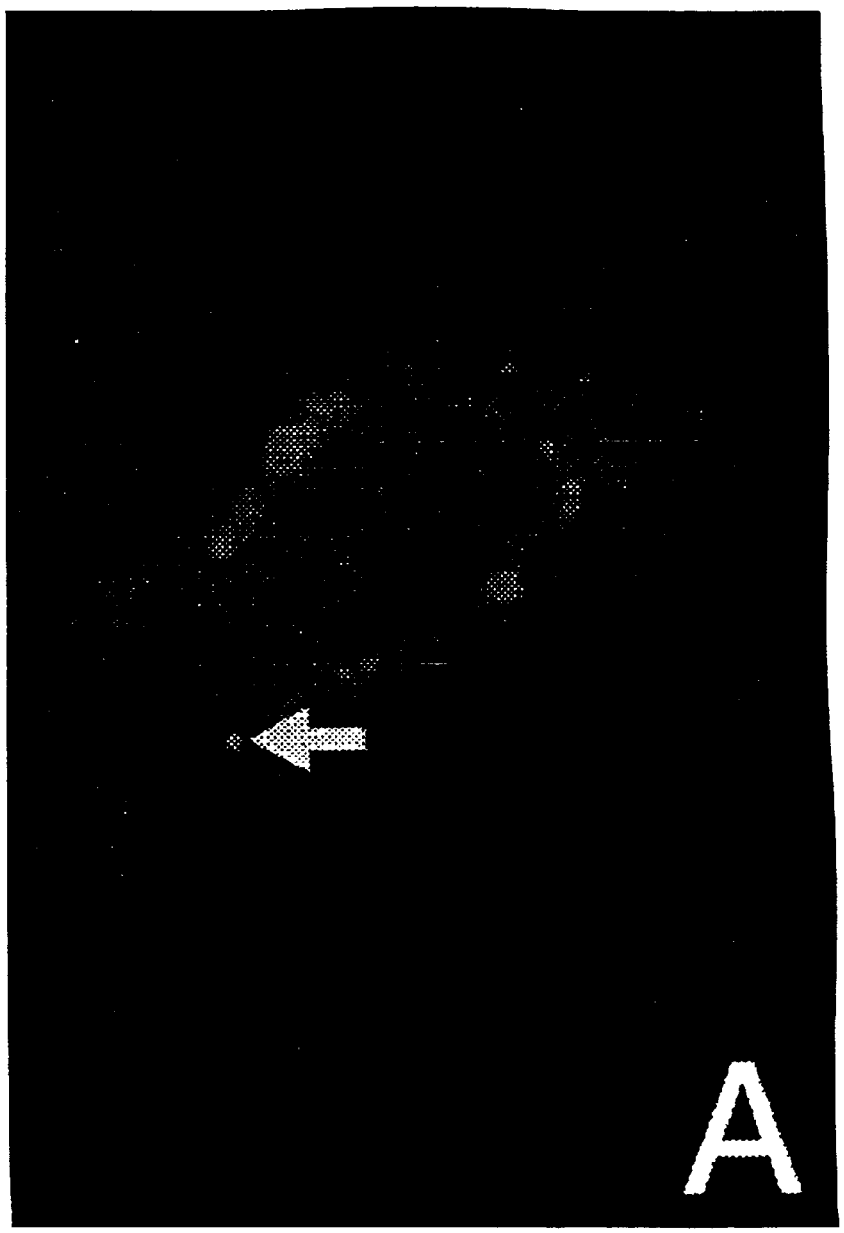
FIG. 5. Immunohistochemical detection of ORF29p in hNTs. hNTs treated with VZV-infected cell supernatants and LysoTracker were analyzed by immunohistochemistry for the presence of ORF29p. Gray arrows indicate ORF29p (A), LysoTracker (B), and colocalization of ORF29p and LysoTracker in the merged image (C). White arrows indicate an endocytic vesicle that does not contain ORF29p (B and C). ORF29p is restricted to cyptoplasmic vesicles in the treated hNTs (D). Untreated hNTs do not contain ORF29p (E).
Figure 5B:
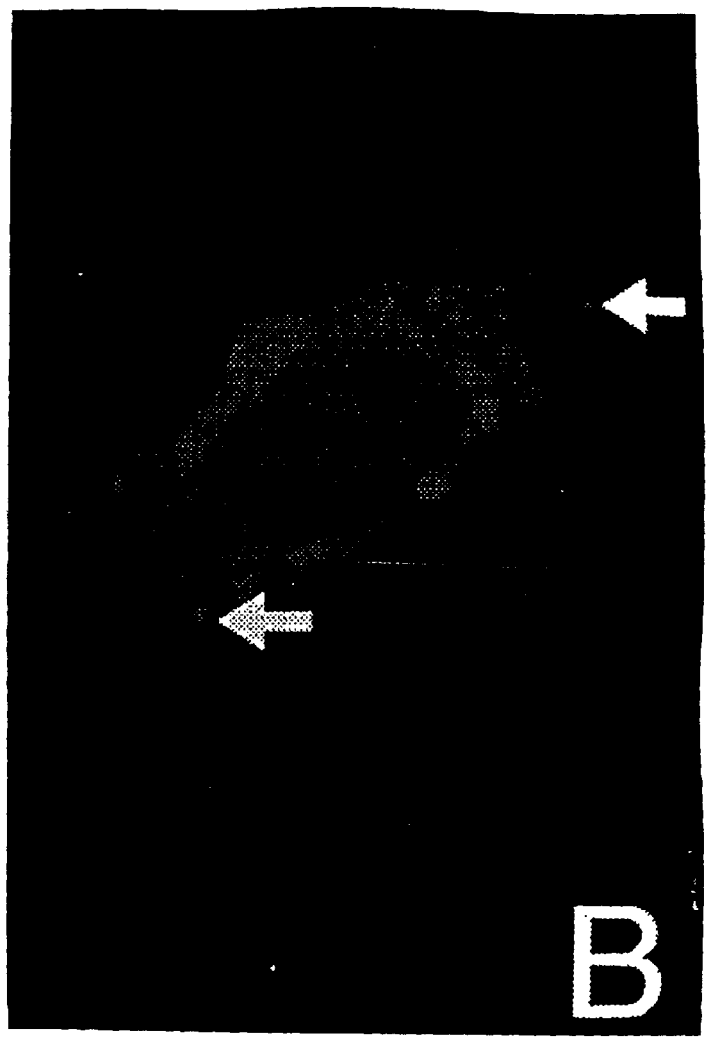
Figure 5C:
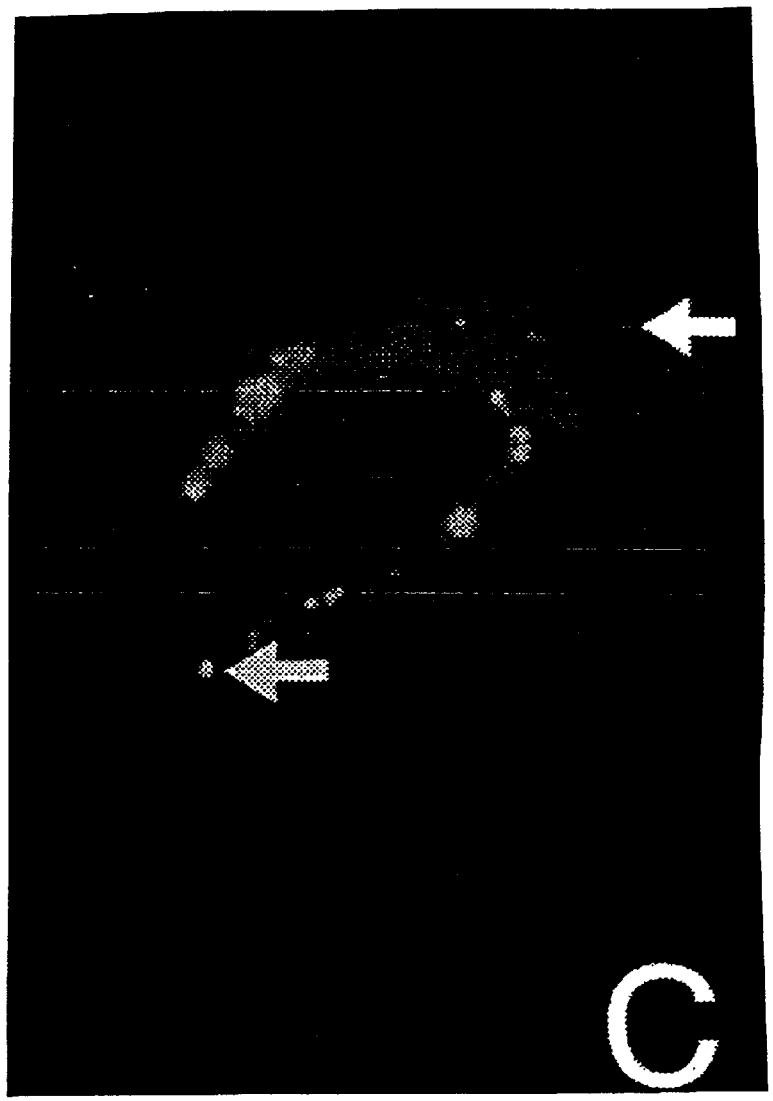
Figure 5D:
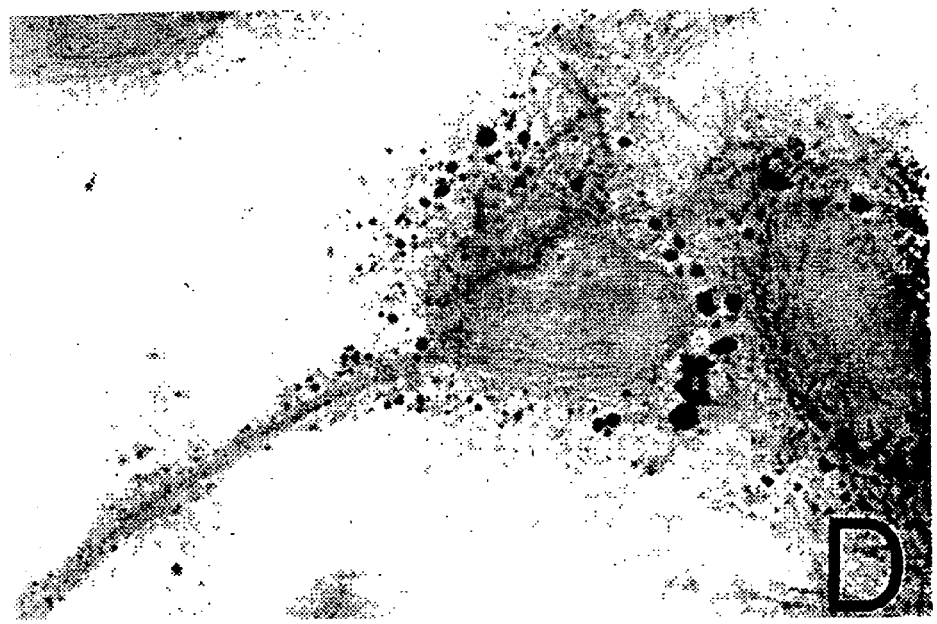
Figure 5E:
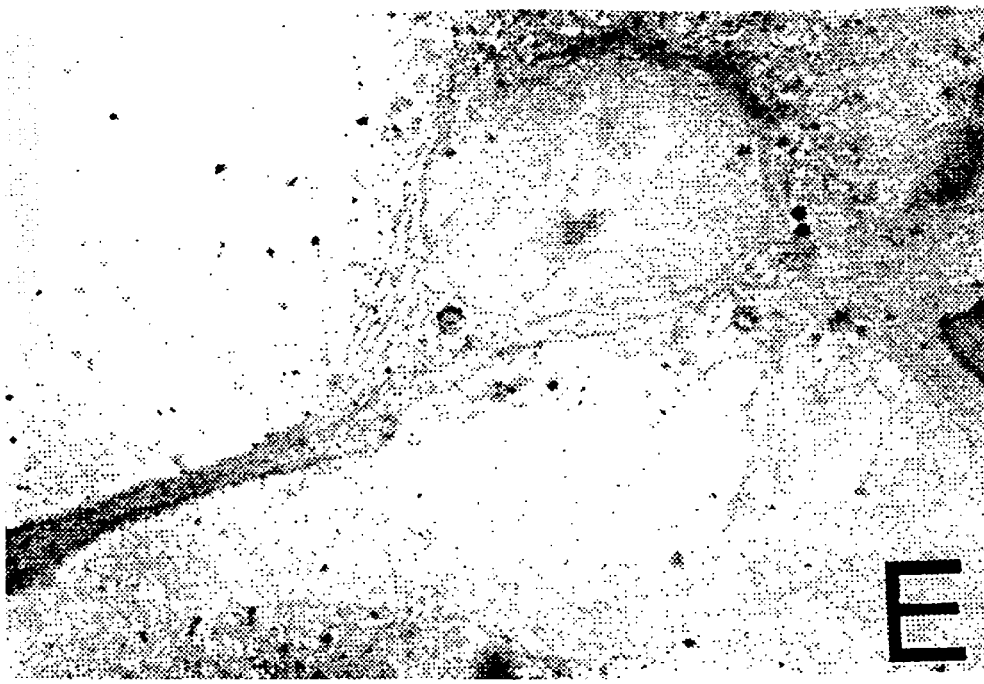

Endocytosis of secreted ORF29p by neurons in tissue culture. Filtered tissue culture medium from VZV-infected HELF and LysoTracker Red DND-99 (Molecular Probes, Eugene, Oreg.), a label for acidic endocytic vesicles, were applied to cultivated human neurons (hNTs) (Stratagene, La Jolla, Calif.) to determine if secreted ORF29p entered neurons by endocytosis. After incubating the hNTs with the filtered culture medium and LysoTracker for 2 h, the cells were examined by immunohistochemistry for the presence of ORF29p. ORF29p was detected in cytoplasmic vesicles (FIGS. 5A and D) that colocalized with LysoTracker (FIG. 5C). ORF29p was not found in untreated hNTs (FIG. 5E). Therefore, extracellular ORF29p can enter hNTs by endocytosis, supporting our hypothesis that the presence of this protein in peripheral axons may result from its assimilation from surrounding cells that are infected with VZV.

Our results illustrate key steps of VZV pathogenesis. During chickenpox, VZV infects epithelial cells, endothelial cells, cells of the monocyte/macrophage lineage, and nerves of the skin. After infecting the neuron, the virus enters latency. In some individuals, the virus reactivates in one or more neurons, travels via the axon to the skin, and infects the epithelial cells.

In addition, endothelial cells are infected in zoster, which could potentially spread virus to other areas. That VZV does not typically spread outside of the dermatome during zoster implies that host immunity effectively halts cell-to-cell spread. This study suggests that entry of VZV into the nervous system during primary infection may not rely solely on axonal transport of mature virions from the skin during chickenpox, because ORF29p was present in axons early in the course of the rash.

REFERENCES

1. Annunziato, P., O. Lungu, A. Gershon, D. Silvers, P. LaRussa, and S. Silverstein. 1996. In situ hybridization detection of varicella zoster virus in paraffin-embedded skin biopsy samples. Clin. Diagn. Virol. 7:69–76.
2. Arvin, A. 1996. Varicella-zoster virus, p. 2547–2585. In B. N. Fields, D. M. Knipe, and P. M. Howley (ed.), Fields virology, 3rd ed., vol. 2. Lippincott-Raven Publishers, Philadelphia, Pa.
3. Asano, Y., N. Itakura, Y. Hiroishi, S. Hirose, T. Nagai, T. Ozaki, T. Yazaki, Y. Yamanishi, and M. Takahashi. 1985. Viremia is present in incubation period in nonimmuno-compromised children with varicella. J. Pediatr. 106:69–71.
4. Assouline, J. G., M. J. Levin, E. O. Major, B. Forghani, S. Straus, and J. M. Ostrove. 1990. Varicella-zoster virus infection of human astrocytes, Schwann cells, and neurons. Virology 179:834–843.
5. Cohen, J., and S. Straus. 1996. Varicella-zoster virus and its replication, p. 2525–2546. In B. N. Fields, D. M. Knipe, and P. M. Howley (ed.), Fields virology, 3rd ed., vol. 2. Lippincott-Raven Publishers, Philadelphia, Pa.
6. Cohrs, R. J., M. Barbour, and D. Gilden. 1996. Varicella-zoster virus (VZV) transcription during latency in human ganglia: detection of transcripts mapping to genes 21, 29, 62, and 63 in a cDNA library enriched for VZV RNA. J.Virol. 70:2789–2796.
7. Cohrs, R. J., M. B. Barbour, R. Mahlingham, M. Wellish, and D. Gilden. 1995. Varicella-zoster virus (VZV) transcription during latency in human ganglia: prevalence of VZV gene 21 transcripts in latently infected human ganglia. J. Virol. 69:2674–2678.
8. Cohrs, R. J., K. Srock, M. B. Barbour, G. Owens, R. Mahlingham, M. Devlin, M. Wellish, and D. Gilden. 1994. Varicella-zoster virus (VZV) transcription during latency in human ganglia: construction of a cDNA library from latently infected human trigeminal ganglia and detection of a VZV transcript. J. Virol. 68:7900–7908.
9. Croen, K. D., J. M. Ostrove, L. Y. Dragovic, and S. E. Straus. 1988. Patterns of gene expression and sites of latency in human ganglia are different for varicella-zoster and herpes simplex viruses. Proc. Natl. Acad. Sci. USA 85:9773–9777.
10. Esiri, M., and A. Tomlinson. 1972. Herpes zoster: demonstration of virus in trigeminal nerve and ganglion by immunofluorescence and electron micros-copy. J. Neurol. Sci. 15:35–48.
11. Hope-Simpson, R. E. 1965. The nature of herpes zoster: a long term study and a new hypothesis. Proc. R. Soc. Med. 58:9–20.
12. Kennedy, P., E. Grinfeld, and J. Gow. 1998. Latent varicella-zoster virus is located predominantly in neurons in human trigeminal ganglia. Proc. Natl. Acad. Sci. USA 95:4658–4662.
13. Kinchington, P., J. Hougland, A. Arvin, W. Ruyechan, and J. Hay. 1992. The varicella-zoster virus immediate-early protein IE62 is a major component of virus particles. J. Virol. 66:359–366.
14. Kinchington, P. R., D. Bookey, and S. E. Turse. 1995. The transcriptional regulatory proteins encoded by varicella-zoster virus open reading frames (ORFs) 4 and 63, but not ORF 61, are associated with purified virus particles. J. Virol. 69:4274–4282.

15. Kinchington, P. R., P. Ling, M. Pensiero, W. T. Ruyechan, and J. Hay. 1990. The glycoprotein products of varicella-zoster virus gene 14 and their defective accumulation in a vaccine strain (Oka). J. Virol. 64:4540–4548.

16. Koropchak, C., G. Graham, J. Palmer, M. Winsberg, S. Ting, M. Wallace, C. Prober, and A. Arvin. 1991. Investigation of varicella-zoster virus infection by polymerase chain reaction in the immunocompetent host with acute varicella. J. Infect. Dis. 163:1016–1022.

17. Lungu, O., P. Annunziato, A. Gershon, S. Stegatis, D. Josefson, P. LaRussa, and S. Silverstein. 1995. Reactivated and latent varicella-zoster virus in human dorsal root ganglia. Proc. Natl. Acad. Sci. USA 92:10980–10984.

18. Lungu, O., C. Panagiotidis, P. Annunziato, A. Gershon, and S. Silverstein. 1998. Aberrant intracellular localization of varicella-zoster virus regulatory proteins during latency. Proc. Natl. Acad. Sci. USA 95:7080–7085.

19. Mahalingam, R., M. Wellish, R. Cohrs, S. Debrus, J. Piette, B. Rentier, and D. Gilden. 1996. Expression of protein encoded by varicella-zoster virus open reading frame 63 in latently infected human ganglionic neurons. Proc. Natl. Acad. Sci. USA 93:2122–2124.

20. Mainka, C., B. Fuss, H. Geiger, H. Hofelmayr, and M. Wolff. 1998. Characterization of viremia at different stages of varicella-zoster virus infection. J. Med. Virol. 46:91–98.

21. Mazur, H., and R. Dolin. 1978. Herpes zoster at the NIH: a 20 year experience. Am. J. Med. 65:738–744.

22. Meier, J. L., R. P. Holman, K. D. Croen, J. E. Smialek, and S. E. Straus. 1993. Varicella-zoster virus transcription in human trigeminal ganglia. Virology 193 :193–200.

23. Nikkels, A., P. Delvenne, S. Debrus, C. Sadzot-Delvaux, J. Piette, B. Rentier, and G. Pierard. 1995. Distribution of varicella-zoster virus gpI and gpII and corresponding genome sequences in the skin. J. Med. Virol. 46:91–6.

24. Nikkels, A. F., B. Rentier, and G. E. Pierard. 1997. Chronic varicella-zoster virus skin lesions in patients with human immunodeficiency virus are related to decreased expression of gE and gB. J. Infect. Dis. 176:261–264.

25. Nikkels, A. F., S. Debrus, C. Sadzot-Delvaux, J. Piette, P. Delvenne, B. Rentier, and G. E. Pierard. 1993. Comparative immunohistochemical study of herpes simplex and varicella-zoster infections. Virchows Arch. A 422:121–126.

26. Sadzot-Delvaux, C., M.-P. Merville-Louis, P. Delree, P. Marc, G. Moonen, and B. Rentier. 1990. An in vivo model of varicella-zoster virus latent infection of dorsal root ganglia. J. Neurosci. Res. 26:83–89.

27. Sawyer, M. H., Y. N. Wu, C. J. Chamberlin, C. Burgos, S. K. Brodine, W. A. Bowler, A. LaRocco, E. C. Oldfield, and M. R. Wallace. 1992. Detection of varicella-zoster virus DNA in the oropharynx and blood of patients with varicella. J. Infect. Dis. 166:885–888.

28. Schwartz, J. 1984. Biochemical control mechanisms in synaptic transmissions, p. 121–131. In E. Kandel and J. Schwartz (ed.), Principles of neural science. Elsevier Science Publishing, New York, N.Y.

29. Tyzzer, E. E. 1996. The histology of skin lesions in varicella. J. Med. Res. 14:361–392.

30. Sambrook, J., et al. 1989. Molecular Cloning: A laboratory Manual, 2nd ed. Cold Spring Harbor Laboratory Press.

---

What is claimed is:

1. A composition of matter comprising Varicella-Zoster Virus 29p protein having polypeptide covalently bound its N- or C-terminus, which composition of matter enters a mammalian cell upon contact therewith, and wherein the Varicella-Zoster Virus 29p protein comprises the amino acid sequence set forth in SEQ ID NO:2.

2. A composition of matter comprising a Varicella-Zoster Virus 29p protein having a lipid-soluble moiety covalently bound to its N- or C-terminus, wherein the Varicella-Zoster Virus 29p protein comprises the amino acid sequence set forth in SEQ ID NO:2, and wherein the lipid-soluble moiety permits the 29p protein to be anchored to a lipid membrane.

3. A lipid vesicle comprising the composition of matter of claim 2 anchored thereto via its lipid-soluble moiety, such that the 29p protein is situated on the vesicle's outer surface and facilitates delivery of the vesicle's contents into a eukaryotic cell when the vesicle is contacted therewith.

4. The lipid vesicle of claim 3, wherein vesicle's contents comprise an agent.

* * * * *

SEQUENCE LISTING

```
<160> NUMBER OF SEQ ID NOS: 2

<210> SEQ ID NO 1
<211> LENGTH: 3610
<212> TYPE: DNA
<213> ORGANISM: Varicella zoster
<220> FEATURE:
<221> NAME/KEY: CDS
<222> LOCATION: (1)..(3609)
<223> OTHER INFORMATION:

<400> SEQUENCE: 1 atg gaa aat act cag aag act gtg aca gtg ccc acg ggg ccc ctg ggt       48
Met Glu Asn Thr Gln Lys Thr Val Thr Val Pro Thr Gly Pro Leu Gly
1               5                   10                  15 tac gtt tat gcg tgc cgg gtt gaa gat ttg gat ctg gag gaa att tca       96
Tyr Val Tyr Ala Cys Arg Val Glu Asp Leu Asp Leu Glu Glu Ile Ser
            20                  25                  30 ttt ttg gcc gct cgt agc acg gac tct gat ttg gct tta tta cct ttg      144
Phe Leu Ala Ala Arg Ser Thr Asp Ser Asp Leu Ala Leu Leu Pro Leu
        35                  40                  45 atg cgt aat ttg acc gtg gaa aaa act ttt aca tcc agc ctg gcg gtg      192
Met Arg Asn Leu Thr Val Glu Lys Thr Phe Thr Ser Ser Leu Ala Val
    50                  55                  60 gtt tct gga gca cgc act acg ggt ctt gcc gga gct ggt att acc tta      240
Val Ser Gly Ala Arg Thr Thr Gly Leu Ala Gly Ala Gly Ile Thr Leu
65                  70                  75                  80 aaa ctc act acc agt cat ttc tat cca tct gtc ttt gtc ttt cac gga      288
```

-continued

```
Lys Leu Thr Thr Ser His Phe Tyr Pro Ser Val Phe Val Phe His Gly
                85                  90                  95 ggc aaa cac gtt tta ccc agc tcc gcg gcc cca aat ctc aca cgc gcg      336
Gly Lys His Val Leu Pro Ser Ser Ala Ala Pro Asn Leu Thr Arg Ala
            100                 105                 110 tgt aac gcg gct cga gaa cgg ttt ggg ttt tca cgc tgc caa ggg cct      384
Cys Asn Ala Ala Arg Glu Arg Phe Gly Phe Ser Arg Cys Gln Gly Pro
        115                 120                 125 cct gtt gac ggt gct gtt gag acg acc ggc gct gag ata tgc acc cgc      432
Pro Val Asp Gly Ala Val Glu Thr Thr Gly Ala Glu Ile Cys Thr Arg
    130                 135                 140 ctt gga tta gag cca gaa aat aca ata tta tac ttg gtg gtc acg gca      480
Leu Gly Leu Glu Pro Glu Asn Thr Ile Leu Tyr Leu Val Val Thr Ala
145                 150                 155                 160 ttg ttt aag gaa gcc gta ttt atg tgc aac gtg ttt ctg cat tat gga      528
Leu Phe Lys Glu Ala Val Phe Met Cys Asn Val Phe Leu His Tyr Gly
                165                 170                 175 gga ctc gat att gtt cat att aac cat ggg gat gtt ata cgt ata ccg      576
Gly Leu Asp Ile Val His Ile Asn His Gly Asp Val Ile Arg Ile Pro
            180                 185                 190 tta ttt ccg gta caa ctt ttc atg ccc gat gtt aac cgt ctg gta ccc      624
Leu Phe Pro Val Gln Leu Phe Met Pro Asp Val Asn Arg Leu Val Pro
        195                 200                 205 gac cca ttc aac act cat cac agg tct atc gga gag ggt ttt gta tac      672
Asp Pro Phe Asn Thr His His Arg Ser Ile Gly Glu Gly Phe Val Tyr
    210                 215                 220 cca aca ccc ttt tat aac acc ggg ttg tgc cat tta ata cat gac tgt      720
Pro Thr Pro Phe Tyr Asn Thr Gly Leu Cys His Leu Ile His Asp Cys
225                 230                 235                 240 gtt att gct ccc atg gcc gtt gcc ttg cgc gtc aga aat gta act gcc      768
Val Ile Ala Pro Met Ala Val Ala Leu Arg Val Arg Asn Val Thr Ala
                245                 250                 255 gtc gcc cga gga gcg gcc cac ctt gct ttt gat gaa aat cac gag ggg      816
Val Ala Arg Gly Ala Ala His Leu Ala Phe Asp Glu Asn His Glu Gly
            260                 265                 270 gca gta ctc ccc cct gac att acg tac acg tat ttt cag tcc tct tca      864
Ala Val Leu Pro Pro Asp Ile Thr Tyr Thr Tyr Phe Gln Ser Ser Ser
        275                 280                 285 agt gga acc act acc gcc cgt gga gcg cgt cga aac gat gtc aac tcc      912
Ser Gly Thr Thr Thr Ala Arg Gly Ala Arg Arg Asn Asp Val Asn Ser
    290                 295                 300 acg tct aag cct agc cca tcg ggg ggt ttt gaa aga cgg ttg gcg tct      960
Thr Ser Lys Pro Ser Pro Ser Gly Gly Phe Glu Arg Arg Leu Ala Ser
305                 310                 315                 320 att atg gcc gct gac aca gcc ttg cac gca gaa gtt ata ttc aac act     1008
Ile Met Ala Ala Asp Thr Ala Leu His Ala Glu Val Ile Phe Asn Thr
                325                 330                 335 gga att tac gaa gaa act cca aca gat atc aaa gaa tgg cca atg ttt     1056
Gly Ile Tyr Glu Glu Thr Pro Thr Asp Ile Lys Glu Trp Pro Met Phe
            340                 345                 350 ata ggc atg gag ggc act ttg cca agg cta aac gct ctg ggg tca tat     1104
Ile Gly Met Glu Gly Thr Leu Pro Arg Leu Asn Ala Leu Gly Ser Tyr
        355                 360                 365 acc gct cgt gtg gcc ggg gtc att ggt gcg atg gtt ttc agc cca aat     1152
Thr Ala Arg Val Ala Gly Val Ile Gly Ala Met Val Phe Ser Pro Asn
    370                 375                 380 tct gcg ttg tat cta act gag gtg gag gat agc ggg atg acc gaa gcc     1200
Ser Ala Leu Tyr Leu Thr Glu Val Glu Asp Ser Gly Met Thr Glu Ala
385                 390                 395                 400
```

```
aag gat ggg gga ccg ggt cca tca ttt aat cga ttt tac cag ttt gcc      1248
Lys Asp Gly Gly Pro Gly Pro Ser Phe Asn Arg Phe Tyr Gln Phe Ala
                405                 410                 415 gga cct cat tta gct gcg aat ccc caa aca gat cga gat ggc cac gtt      1296
Gly Pro His Leu Ala Ala Asn Pro Gln Thr Asp Arg Asp Gly His Val
        420                 425                 430 cta tcc agt cag tct acg ggt tca tca aac aca gag ttt agc gtg gat      1344
Leu Ser Ser Gln Ser Thr Gly Ser Ser Asn Thr Glu Phe Ser Val Asp
    435                 440                 445 tat ttg gca ctc att tgt gga ttt gga gca ccc ctg ttg gcg cga ctg      1392
Tyr Leu Ala Leu Ile Cys Gly Phe Gly Ala Pro Leu Leu Ala Arg Leu
450                 455                 460 ctt ttt tat cta gaa cgc tgt gac gct ggt gcg ttt aca ggg ggt cac      1440
Leu Phe Tyr Leu Glu Arg Cys Asp Ala Gly Ala Phe Thr Gly Gly His
465                 470                 475                 480 ggg gat gcg tta aaa tat gtt acg ggg acc ttt gac tct gaa att cca      1488
Gly Asp Ala Leu Lys Tyr Val Thr Gly Thr Phe Asp Ser Glu Ile Pro
                485                 490                 495 tgt agt tta tgt gaa aaa cac acg cgg ccg gta tgc gct cac aca aca      1536
Cys Ser Leu Cys Glu Lys His Thr Arg Pro Val Cys Ala His Thr Thr
            500                 505                 510 gta cac cga ctt aga caa cgc atg ccg cga ttt gga caa gcc acc cgt      1584
Val His Arg Leu Arg Gln Arg Met Pro Arg Phe Gly Gln Ala Thr Arg
        515                 520                 525 caa cct att ggg gtg ttt gga aca atg aac agc caa tat agc gac tgc      1632
Gln Pro Ile Gly Val Phe Gly Thr Met Asn Ser Gln Tyr Ser Asp Cys
    530                 535                 540 gat cct cta gga aac tat gct cca tat tta atc ctt cga aaa ccc ggg      1680
Asp Pro Leu Gly Asn Tyr Ala Pro Tyr Leu Ile Leu Arg Lys Pro Gly
545                 550                 555                 560 gat caa acg gaa gca gca aag gca acc atg cag gac act tat agg gct      1728
Asp Gln Thr Glu Ala Ala Lys Ala Thr Met Gln Asp Thr Tyr Arg Ala
                565                 570                 575 aca cta gaa cgc ttg ttt atc gat cta gaa caa gag cga cta ctg gat      1776
Thr Leu Glu Arg Leu Phe Ile Asp Leu Glu Gln Glu Arg Leu Leu Asp
            580                 585                 590 cgc ggt gcc cca tgt tct tcc gag gga cta tcg tct gtc att gtg gat      1824
Arg Gly Ala Pro Cys Ser Ser Glu Gly Leu Ser Ser Val Ile Val Asp
        595                 600                 605 cat cca acg ttt cgt cgc ata tta gac aca ctg cgt gcg cgt ata gaa      1872
His Pro Thr Phe Arg Arg Ile Leu Asp Thr Leu Arg Ala Arg Ile Glu
    610                 615                 620 cag aca aca aca caa ttt atg aaa gtg ttg gtt gag acc cgc gat tat      1920
Gln Thr Thr Thr Gln Phe Met Lys Val Leu Val Glu Thr Arg Asp Tyr
625                 630                 635                 640 aag atc cgt gaa gga tta tcc gaa gcc acc cat tca atg gcg tta acg      1968
Lys Ile Arg Glu Gly Leu Ser Glu Ala Thr His Ser Met Ala Leu Thr
                645                 650                 655 ttt gat cca tac tca gga gca ttt tgt ccc att acc aat ttt tta gtt      2016
Phe Asp Pro Tyr Ser Gly Ala Phe Cys Pro Ile Thr Asn Phe Leu Val
            660                 665                 670 aaa cga aca cac cta gcc gtg gta caa gac tta gca tta agc caa tgt      2064
Lys Arg Thr His Leu Ala Val Val Gln Asp Leu Ala Leu Ser Gln Cys
        675                 680                 685 cat tgt gta ttt tac gga cag caa gtt gag ggg cgg aac ttt cgt aac      2112
His Cys Val Phe Tyr Gly Gln Gln Val Glu Gly Arg Asn Phe Arg Asn
    690                 695                 700 caa ttc caa cct gtt ttg cgg cgg cgt ttt gtt gac ctg ttt aat ggg      2160
Gln Phe Gln Pro Val Leu Arg Arg Arg Phe Val Asp Leu Phe Asn Gly
705                 710                 715                 720
```

```
                                                 -continued ggg ttt ata tca aca cgc tct ata acc gta aca tta tct gaa ggt cct   2208
Gly Phe Ile Ser Thr Arg Ser Ile Thr Val Thr Leu Ser Glu Gly Pro
                725                 730                 735 gta tcc gcc cca aat ccg aca ttg gga caa gac gcg ccc gcg ggg cgt   2256
Val Ser Ala Pro Asn Pro Thr Leu Gly Gln Asp Ala Pro Ala Gly Arg
            740                 745                 750 acc ttt gat ggg gat tta gcg cgc gta agc gtg gaa gtt att cgg gat   2304
Thr Phe Asp Gly Asp Leu Ala Arg Val Ser Val Glu Val Ile Arg Asp
        755                 760                 765 ata cga gtt aaa aat agg gtc gtt ttt tca ggt aac tgt aca aat ctc   2352
Ile Arg Val Lys Asn Arg Val Val Phe Ser Gly Asn Cys Thr Asn Leu
    770                 775                 780 tct gag gca gcc cgg gca agg ctt gta ggc ctt gca agt gca tac caa   2400
Ser Glu Ala Ala Arg Ala Arg Leu Val Gly Leu Ala Ser Ala Tyr Gln
785                 790                 795                 800 cgc caa gaa aaa aga gtg gat atg tta cac ggg gcc cta ggg ttt ttg   2448
Arg Gln Glu Lys Arg Val Asp Met Leu His Gly Ala Leu Gly Phe Leu
                805                 810                 815 ctt aaa cag ttt cac ggc ctg tta ttt cct cgg ggt atg cca cca aac   2496
Leu Lys Gln Phe His Gly Leu Leu Phe Pro Arg Gly Met Pro Pro Asn
            820                 825                 830 agt aaa tcc ccc aac ccg cag tgg ttt tgg acc ctg tta caa cgc aac   2544
Ser Lys Ser Pro Asn Pro Gln Trp Phe Trp Thr Leu Leu Gln Arg Asn
        835                 840                 845 cag atg ccg gca gat aaa ctt aca cac gaa gag att acc act att gca   2592
Gln Met Pro Ala Asp Lys Leu Thr His Glu Glu Ile Thr Thr Ile Ala
    850                 855                 860 gct gtt aaa cgg ttt acc gag gaa tat gca gca ata aac ttt att aat   2640
Ala Val Lys Arg Phe Thr Glu Glu Tyr Ala Ala Ile Asn Phe Ile Asn
865                 870                 875                 880 cta ccc cca acc tgc ata gga gaa tta gcc cag ttt tat atg gca aat   2688
Leu Pro Pro Thr Cys Ile Gly Glu Leu Ala Gln Phe Tyr Met Ala Asn
                885                 890                 895 ctt att ctt aaa tac tgc gat cat tca cag tac ctt ata aat acc tta   2736
Leu Ile Leu Lys Tyr Cys Asp His Ser Gln Tyr Leu Ile Asn Thr Leu
            900                 905                 910 act tct ata att acg ggt gcc agg cgc ccg cgt gac cca tca tcc gtt   2784
Thr Ser Ile Ile Thr Gly Ala Arg Arg Pro Arg Asp Pro Ser Ser Val
        915                 920                 925 ttg cat tgg att cgt aaa gat gtc acg tcc gcc gcg gac ata gaa acc   2832
Leu His Trp Ile Arg Lys Asp Val Thr Ser Ala Ala Asp Ile Glu Thr
    930                 935                 940 caa gca aag gcg ctt ctt gaa aaa acg gaa aac tta ccg gaa tta tgg   2880
Gln Ala Lys Ala Leu Leu Glu Lys Thr Glu Asn Leu Pro Glu Leu Trp
945                 950                 955                 960 act acg gct ttt act tca act cat tta gtc cgc gcg gcc atg aat caa   2928
Thr Thr Ala Phe Thr Ser Thr His Leu Val Arg Ala Ala Met Asn Gln
                965                 970                 975 cgt ccc atg gtc gtt tta gga ata agc att agt aaa tat cac gga gcg   2976
Arg Pro Met Val Val Leu Gly Ile Ser Ile Ser Lys Tyr His Gly Ala
            980                 985                 990 gca gga aac aac cgc gtc ttt cag  gca ggg aat tgg agc  ggt tta aac  3024
Ala Gly Asn Asn Arg Val Phe Gln  Ala Gly Asn Trp Ser  Gly Leu Asn
        995                 1000                1005 ggg ggt  aaa aat gta tgc ccg  cta ttt aca ttt gat  cgc act cgc     3069
Gly Gly  Lys Asn Val Cys Pro  Leu Phe Thr Phe Asp  Arg Thr Arg
    1010                1015                1020 cgt ttt  ata ata gca tgt cct  aga gga ggt ttt atc  tgc ccc gta     3114
Arg Phe  Ile Ile Ala Cys Pro  Arg Gly Gly Phe Ile  Cys Pro Val
```

-continued

```
                        1025                    1030                    1035
       aca ggt ccc tcg tcg gga aat cga gaa acc acc cta tcc gac caa        3159
       Thr Gly Pro Ser Ser Gly Asn Arg Glu Thr Thr Leu Ser Asp Gln
           1040                    1045                    1050 gtt cgc ggt ata att gtc agt ggc ggg gcc atg gtt caa tta gcc        3204
       Val Arg Gly Ile Ile Val Ser Gly Gly Ala Met Val Gln Leu Ala
           1055                    1060                    1065 ata tac gcc acg gtt gtg cgt gca gtg ggc gct cga gca caa cat        3249
       Ile Tyr Ala Thr Val Val Arg Ala Val Gly Ala Arg Ala Gln His
           1070                    1075                    1080 atg gca ttt gac gac tgg tta agt ctt aca gac gat gag ttt tta        3294
       Met Ala Phe Asp Asp Trp Leu Ser Leu Thr Asp Asp Glu Phe Leu
           1085                    1090                    1095 gcc aga gac ttg gag gag tta cac gac cag att atc caa acc ctg        3339
       Ala Arg Asp Leu Glu Glu Leu His Asp Gln Ile Ile Gln Thr Leu
           1100                    1105                    1110 gaa acg ccc tgg acc gta gaa ggc gct cta gaa gca gta aag att        3384
       Glu Thr Pro Trp Thr Val Glu Gly Ala Leu Glu Ala Val Lys Ile
           1115                    1120                    1125 cta gat gaa aaa acg aca gcg gga gat ggg gaa acc ccc aca aac        3429
       Leu Asp Glu Lys Thr Thr Ala Gly Asp Gly Glu Thr Pro Thr Asn
           1130                    1135                    1140 cta gca ttt aat ttt gat tct tgt gaa cca agc cat gac acc aca        3474
       Leu Ala Phe Asn Phe Asp Ser Cys Glu Pro Ser His Asp Thr Thr
           1145                    1150                    1155 tct aac gta tta aac att tca ggg tca aac att tca ggg tca act        3519
       Ser Asn Val Leu Asn Ile Ser Gly Ser Asn Ile Ser Gly Ser Thr
           1160                    1165                    1170 gtc cct ggt ctt aaa cga ccc ccc gaa gat gac gaa ctc ttt gat        3564
       Val Pro Gly Leu Lys Arg Pro Pro Glu Asp Asp Glu Leu Phe Asp
           1175                    1180                    1185 ctt agt ggt att ccc ata aaa cat ggg aac att aca atg gaa atg a     3610
       Leu Ser Gly Ile Pro Ile Lys His Gly Asn Ile Thr Met Glu Met
           1190                    1195                    1200

<210> SEQ ID NO 2
<211> LENGTH: 1203
<212> TYPE: PRT
<213> ORGANISM: Varicella zoster

<400> SEQUENCE: 2

Met Glu Asn Thr Gln Lys Thr Val Thr Val Pro Thr Gly Pro Leu Gly
1               5                   10                  15

Tyr Val Tyr Ala Cys Arg Val Glu Asp Leu Asp Leu Glu Glu Ile Ser
            20                  25                  30

Phe Leu Ala Ala Arg Ser Thr Asp Ser Asp Leu Ala Leu Leu Pro Leu
        35                  40                  45

Met Arg Asn Leu Thr Val Glu Lys Thr Phe Thr Ser Ser Leu Ala Val
    50                  55                  60

Val Ser Gly Ala Arg Thr Thr Gly Leu Ala Gly Ala Gly Ile Thr Leu
65                  70                  75                  80

Lys Leu Thr Thr Ser His Phe Tyr Pro Ser Val Phe Val Phe His Gly
                85                  90                  95

Gly Lys His Val Leu Pro Ser Ser Ala Ala Pro Asn Leu Thr Arg Ala
            100                 105                 110

Cys Asn Ala Ala Arg Glu Arg Phe Gly Phe Ser Arg Cys Gln Gly Pro
        115                 120                 125

Pro Val Asp Gly Ala Val Glu Thr Thr Gly Ala Glu Ile Cys Thr Arg
```

-continued

```
            130                 135                 140
Leu Gly Leu Glu Pro Glu Asn Thr Ile Leu Tyr Leu Val Val Thr Ala
145                 150                 155                 160

Leu Phe Lys Glu Ala Val Phe Met Cys Asn Val Phe Leu His Tyr Gly
                165                 170                 175

Gly Leu Asp Ile Val His Ile Asn His Gly Asp Val Ile Arg Ile Pro
                180                 185                 190

Leu Phe Pro Val Gln Leu Phe Met Pro Asp Val Asn Arg Leu Val Pro
                195                 200                 205

Asp Pro Phe Asn Thr His His Arg Ser Ile Gly Glu Gly Phe Val Tyr
210                 215                 220

Pro Thr Pro Phe Tyr Asn Thr Gly Leu Cys His Leu Ile His Asp Cys
225                 230                 235                 240

Val Ile Ala Pro Met Ala Val Ala Leu Arg Val Arg Asn Val Thr Ala
                245                 250                 255

Val Ala Arg Gly Ala Ala His Leu Ala Phe Asp Glu Asn His Glu Gly
                260                 265                 270

Ala Val Leu Pro Pro Asp Ile Thr Tyr Thr Tyr Phe Gln Ser Ser Ser
                275                 280                 285

Ser Gly Thr Thr Thr Ala Arg Gly Ala Arg Arg Asn Asp Val Asn Ser
                290                 295                 300

Thr Ser Lys Pro Ser Pro Ser Gly Gly Phe Glu Arg Arg Leu Ala Ser
305                 310                 315                 320

Ile Met Ala Ala Asp Thr Ala Leu His Ala Glu Val Ile Phe Asn Thr
                325                 330                 335

Gly Ile Tyr Glu Glu Thr Pro Thr Asp Ile Lys Glu Trp Pro Met Phe
                340                 345                 350

Ile Gly Met Glu Gly Thr Leu Pro Arg Leu Asn Ala Leu Gly Ser Tyr
                355                 360                 365

Thr Ala Arg Val Ala Gly Val Ile Gly Ala Met Val Phe Ser Pro Asn
                370                 375                 380

Ser Ala Leu Tyr Leu Thr Glu Val Glu Asp Ser Gly Met Thr Glu Ala
385                 390                 395                 400

Lys Asp Gly Gly Pro Gly Pro Ser Phe Asn Arg Phe Tyr Gln Phe Ala
                405                 410                 415

Gly Pro His Leu Ala Ala Asn Pro Gln Thr Asp Arg Asp Gly His Val
                420                 425                 430

Leu Ser Ser Gln Ser Thr Gly Ser Ser Asn Thr Glu Phe Ser Val Asp
                435                 440                 445

Tyr Leu Ala Leu Ile Cys Gly Phe Gly Ala Pro Leu Leu Ala Arg Leu
450                 455                 460

Leu Phe Tyr Leu Glu Arg Cys Asp Ala Gly Ala Phe Thr Gly Gly His
465                 470                 475                 480

Gly Asp Ala Leu Lys Tyr Val Thr Gly Thr Phe Asp Ser Glu Ile Pro
                485                 490                 495

Cys Ser Leu Cys Glu Lys His Thr Arg Pro Val Cys Ala His Thr Thr
                500                 505                 510

Val His Arg Leu Arg Gln Arg Met Pro Arg Phe Gly Gln Ala Thr Arg
                515                 520                 525

Gln Pro Ile Gly Val Phe Gly Thr Met Asn Ser Gln Tyr Ser Asp Cys
                530                 535                 540

Asp Pro Leu Gly Asn Tyr Ala Pro Tyr Leu Ile Leu Arg Lys Pro Gly
545                 550                 555                 560
```

```
Asp Gln Thr Glu Ala Ala Lys Ala Thr Met Gln Asp Thr Tyr Arg Ala
            565                 570                 575
Thr Leu Glu Arg Leu Phe Ile Asp Leu Glu Gln Glu Arg Leu Leu Asp
            580                 585                 590
Arg Gly Ala Pro Cys Ser Ser Glu Gly Leu Ser Ser Val Ile Val Asp
            595                 600                 605
His Pro Thr Phe Arg Arg Ile Leu Asp Thr Leu Arg Ala Arg Ile Glu
            610                 615                 620
Gln Thr Thr Thr Gln Phe Met Lys Val Leu Val Glu Thr Arg Asp Tyr
625                 630                 635                 640
Lys Ile Arg Glu Gly Leu Ser Glu Ala Thr His Ser Met Ala Leu Thr
            645                 650                 655
Phe Asp Pro Tyr Ser Gly Ala Phe Cys Pro Ile Thr Asn Phe Leu Val
            660                 665                 670
Lys Arg Thr His Leu Ala Val Val Gln Asp Leu Ala Leu Ser Gln Cys
            675                 680                 685
His Cys Val Phe Tyr Gly Gln Gln Val Glu Gly Arg Asn Phe Arg Asn
            690                 695                 700
Gln Phe Gln Pro Val Leu Arg Arg Arg Phe Val Asp Leu Phe Asn Gly
705                 710                 715                 720
Gly Phe Ile Ser Thr Arg Ser Ile Thr Val Thr Leu Ser Glu Gly Pro
            725                 730                 735
Val Ser Ala Pro Asn Pro Thr Leu Gly Gln Asp Ala Pro Ala Gly Arg
            740                 745                 750
Thr Phe Asp Gly Asp Leu Ala Arg Val Ser Val Glu Val Ile Arg Asp
            755                 760                 765
Ile Arg Val Lys Asn Arg Val Val Phe Ser Gly Asn Cys Thr Asn Leu
            770                 775                 780
Ser Glu Ala Ala Arg Ala Arg Leu Val Gly Leu Ala Ser Ala Tyr Gln
785                 790                 795                 800
Arg Gln Glu Lys Arg Val Asp Met Leu His Gly Ala Leu Gly Phe Leu
            805                 810                 815
Leu Lys Gln Phe His Gly Leu Leu Phe Pro Arg Gly Met Pro Pro Asn
            820                 825                 830
Ser Lys Ser Pro Asn Pro Gln Trp Phe Trp Thr Leu Leu Gln Arg Asn
            835                 840                 845
Gln Met Pro Ala Asp Lys Leu Thr His Glu Glu Ile Thr Thr Ile Ala
850                 855                 860
Ala Val Lys Arg Phe Thr Glu Glu Tyr Ala Ala Ile Asn Phe Ile Asn
865                 870                 875                 880
Leu Pro Pro Thr Cys Ile Gly Glu Leu Ala Gln Phe Tyr Met Ala Asn
            885                 890                 895
Leu Ile Leu Lys Tyr Cys Asp His Ser Gln Tyr Leu Ile Asn Thr Leu
            900                 905                 910
Thr Ser Ile Ile Thr Gly Ala Arg Arg Pro Arg Asp Pro Ser Ser Val
            915                 920                 925
Leu His Trp Ile Arg Lys Asp Val Thr Ser Ala Ala Asp Ile Glu Thr
            930                 935                 940
Gln Ala Lys Ala Leu Leu Glu Lys Thr Glu Asn Leu Pro Glu Leu Trp
945                 950                 955                 960
Thr Thr Ala Phe Thr Ser Thr His Leu Val Arg Ala Ala Met Asn Gln
            965                 970                 975
```

-continued

```
Arg Pro Met Val Val Leu Gly Ile Ser Ile Ser Lys Tyr His Gly Ala
            980                 985                 990

Ala Gly Asn Asn Arg Val Phe Gln Ala Gly Asn Trp Ser  Gly Leu Asn
            995                1000                1005

Gly Gly Lys Asn Val Cys Pro Leu Phe Thr Phe Asp  Arg Thr Arg
    1010                1015                1020

Arg Phe Ile Ile Ala Cys Pro Arg Gly Gly Phe Ile  Cys Pro Val
    1025                1030                1035

Thr Gly Pro Ser Ser Gly Asn Arg Glu Thr Thr Leu  Ser Asp Gln
    1040                1045                1050

Val Arg Gly Ile Ile Val Ser Gly Gly Ala Met Val  Gln Leu Ala
    1055                1060                1065

Ile Tyr Ala Thr Val Val Arg Ala Val Gly Ala Arg  Ala Gln His
    1070                1075                1080

Met Ala Phe Asp Asp Trp Leu Ser Leu Thr Asp Asp  Glu Phe Leu
    1085                1090                1095

Ala Arg Asp Leu Glu Glu Leu His Asp Gln Ile Ile  Gln Thr Leu
    1100                1105                1110

Glu Thr Pro Trp Thr Val Glu Gly Ala Leu Glu Ala  Val Lys Ile
    1115                1120                1125

Leu Asp Glu Lys Thr Thr Ala Gly Asp Gly Glu Thr  Pro Thr Asn
    1130                1135                1140

Leu Ala Phe Asn Phe Asp Ser Cys Glu Pro Ser His  Asp Thr Thr
    1145                1150                1155

Ser Asn Val Leu Asn Ile Ser Gly Ser Asn Ile Ser  Gly Ser Thr
    1160                1165                1170

Val Pro Gly Leu Lys Arg Pro Pro Glu Asp Asp Glu  Leu Phe Asp
    1175                1180                1185

Leu Ser Gly Ile Pro Ile Lys His Gly Asn Ile Thr  Met Glu Met
    1190                1195                1200
```